(12) United States Patent
Horchner et al.

(10) Patent No.: US 7,248,360 B2
(45) Date of Patent: Jul. 24, 2007

(54) POLYCHRONIC LASER SCANNING SYSTEM AND METHOD OF USE

(75) Inventors: Uwe Horchner, Woodside, CA (US); Aaron B. Kantor, San Carlos, CA (US)

(73) Assignee: PPD Biomarker Discovery Sciences, LLC, Wilmington, NC (US)

( * ) Notice: Subject to any disclaimer, the term of this patent is extended or adjusted under 35 U.S.C. 154(b) by 0 days.

(21) Appl. No.: 11/090,673

(22) Filed: Mar. 25, 2005

(65) Prior Publication Data

US 2005/0280817 A1 Dec. 22, 2005

Related U.S. Application Data

(60) Provisional application No. 60/559,322, filed on Apr. 2, 2004.

(51) Int. Cl.
*G01J 3/30* (2006.01)
*G01J 3/28* (2006.01)
*G01J 3/44* (2006.01)
*G01J 3/40* (2006.01)
*G01J 1/58* (2006.01)
*F21V 9/16* (2006.01)
*G01T 1/10* (2006.01)
*G21H 3/02* (2006.01)
*G21K 5/00* (2006.01)
*H01J 65/06* (2006.01)
*H01J 65/08* (2006.01)

(52) U.S. Cl. ............... 356/318; 356/301; 356/302; 356/303; 356/317; 356/326; 356/328; 250/458.1; 250/459.1

(58) Field of Classification Search ............ None
See application file for complete search history.

(56) References Cited

U.S. PATENT DOCUMENTS 3,552,865 A 1/1971 Leung et al.

(Continued)

FOREIGN PATENT DOCUMENTS

DE 19829094 1/2000

(Continued)

OTHER PUBLICATIONS

Kantor et al., 2004, "Immune Systems Biology: Immunoprofiling of Cells and Molecules," *BioTechniques*, 36(3):520-524.

(Continued)

*Primary Examiner*—Gregory J. Toatley, Jr.
*Assistant Examiner*—Gordon J. Stock, Jr.
(74) *Attorney, Agent, or Firm*—Sheridan Ross P.C.

(57) ABSTRACT

A system for laser scanning provides spectral flexibility needed for the spectroscopic monitoring of highly multiplexed samples, such as cellular and particle assays in whole blood or other suspensions. In accordance with embodiments of the present invention, the system comprises a scanner to direct an excitation laser through a sample, an objective to collect light emitted by the sample in response to the excitation laser, a spectrograph to disperse the emitted light over a plurality of wavelengths as a spectrum, and a charge coupled device for detecting the spectrum. The system can be used with samples having a variety of reporter tags, including one or more SERS tags, fluorescent organic and protein tags, and quantum dot tags. A laser scanning apparatus and method of using the same is also provided.

39 Claims, 7 Drawing Sheets

U.S. PATENT DOCUMENTS

| | | | |
|---|---|---|---|
| 3,690,836 A | 9/1972 | Buissiere et al. | |
| 3,997,298 A | 12/1976 | McLafferty et al. | |
| 3,999,047 A | 12/1976 | Green | |
| 4,405,235 A | 9/1983 | Rossiter | |
| 4,426,451 A | 1/1984 | Columbus | |
| 4,643,570 A | 2/1987 | Machler et al. | |
| 4,752,888 A | 6/1988 | Yoshihara | |
| 4,761,381 A | 8/1988 | Blatt et al. | |
| 4,786,813 A | 11/1988 | Svanberg et al. | |
| 4,844,617 A * | 7/1989 | Kelderman et al. | 356/624 |
| 4,963,498 A | 10/1990 | Hillman et al. | |
| 5,072,382 A | 12/1991 | Kamentsky | |
| 5,091,652 A | 2/1992 | Mathies et al. | |
| 5,119,315 A | 6/1992 | Kemp et al. | |
| 5,127,730 A | 7/1992 | Brelje et al. | |
| 5,192,980 A | 3/1993 | Dixon et al. | |
| 5,239,178 A | 8/1993 | Derndinger et al. | |
| 5,274,240 A | 12/1993 | Mathies et al. | |
| 5,304,810 A | 4/1994 | Amos | |
| 5,377,003 A | 12/1994 | Lewis et al. | |
| 5,412,208 A | 5/1995 | Covey et al. | |
| 5,430,542 A | 7/1995 | Shepherd | |
| 5,446,532 A | 8/1995 | Yamazaki | |
| 5,453,505 A | 9/1995 | Lee et al. | |
| 5,456,252 A | 10/1995 | Vari et al. | |
| D366,938 S | 2/1996 | Shartle et al. | |
| 5,492,833 A * | 2/1996 | Rodriguez et al. | 436/63 |
| 5,523,573 A | 6/1996 | Hanninen et al. | |
| 5,532,873 A * | 7/1996 | Dixon | 359/388 |
| 5,547,849 A | 8/1996 | Baer et al. | |
| 5,556,764 A | 9/1996 | Sizto et al. | |
| 5,578,832 A | 11/1996 | Trulson et al. | |
| 5,585,246 A | 12/1996 | Dubrow et al. | |
| 5,592,402 A | 1/1997 | Beebe et al. | |
| 5,627,041 A | 5/1997 | Shartle | |
| D382,648 S | 8/1997 | Shartle et al. | |
| 5,658,735 A | 8/1997 | Lee | |
| D383,852 S | 9/1997 | Shartle et al. | |
| 5,672,869 A | 9/1997 | Windig et al. | |
| 5,682,038 A | 10/1997 | Hoffman | |
| 5,687,964 A | 11/1997 | Stephan et al. | |
| 5,689,110 A | 11/1997 | Dietz et al. | |
| 5,692,220 A | 11/1997 | Diamond et al. | |
| 5,710,713 A | 1/1998 | Wright et al. | |
| D391,373 S | 2/1998 | Shartle | |
| 5,713,364 A * | 2/1998 | DeBaryshe et al. | 600/476 |
| 5,726,751 A | 3/1998 | Altendorf et al. | |
| 5,734,058 A | 3/1998 | Lee | |
| 5,736,410 A | 4/1998 | Zarling et al. | |
| 5,739,000 A | 4/1998 | Bierre et al. | |
| 5,741,411 A | 4/1998 | Yeung et al. | |
| D395,708 S | 6/1998 | Shartle et al. | |
| 5,795,729 A | 8/1998 | Lee | |
| 5,814,820 A | 9/1998 | Dong et al. | |
| 5,832,826 A | 11/1998 | Mack et al. | |
| 5,867,610 A | 2/1999 | Lee et al. | |
| 5,871,946 A | 2/1999 | Lucas et al. | |
| 5,885,841 A | 3/1999 | Higgs, Jr. et al. | |
| 5,910,287 A | 6/1999 | Cassin et al. | |
| 5,912,134 A | 6/1999 | Shartle | |
| 5,932,428 A | 8/1999 | Dubrow et al. | |
| 5,962,238 A | 10/1999 | Sizto et al. | |
| 5,981,180 A | 11/1999 | Chandler et al. | |
| 5,995,989 A | 11/1999 | Gedcke et al. | |
| 6,002,986 A | 12/1999 | Mito | |
| 6,008,490 A | 12/1999 | Kato | |
| 6,008,896 A | 12/1999 | Sabsabi et al. | |
| 6,017,693 A | 1/2000 | Yates | |
| 6,059,724 A | 5/2000 | Campell | |
| 6,063,338 A | 5/2000 | Pham et al. | |
| 6,066,216 A | 5/2000 | Ruppel, Jr. | |
| 6,072,624 A * | 6/2000 | Dixon et al. | 359/385 |
| 6,091,492 A | 7/2000 | Strickland et al. | |
| 6,093,573 A | 7/2000 | Beamer et al. | |
| 6,104,945 A | 8/2000 | Modell et al. | |
| 6,112,161 A | 8/2000 | Dryden et al. | |
| 6,133,046 A | 10/2000 | Clerc | |
| 6,134,002 A * | 10/2000 | Stimson et al. | 356/326 |
| 6,138,117 A | 10/2000 | Bayardo | |
| 6,147,344 A | 11/2000 | Annis et al. | |
| 6,200,532 B1 | 3/2001 | Wu et al. | |
| 6,207,955 B1 | 3/2001 | Wells et al. | |
| 6,215,892 B1 | 4/2001 | Douglass et al. | |
| 6,229,603 B1 | 5/2001 | Coassin et al. | |
| 6,229,635 B1 | 5/2001 | Wulf | |
| 6,232,114 B1 | 5/2001 | Coassin et al. | |
| 6,236,945 B1 | 5/2001 | Simpson et al. | |
| 6,253,162 B1 | 6/2001 | Jarman et al. | |
| 6,278,794 B1 | 8/2001 | Parekh et al. | |
| 6,334,099 B1 | 12/2001 | Grace et al. | |
| 6,376,843 B1 | 4/2002 | Palo | |
| 6,377,842 B1 | 4/2002 | Pogue et al. | |
| 6,388,788 B1 | 5/2002 | Harris et al. | |
| 6,391,649 B1 | 5/2002 | Chait et al. | |
| 6,400,487 B1 | 6/2002 | Harris et al. | |
| 6,421,612 B1 | 7/2002 | Agrafiotis et al. | |
| 6,449,584 B1 | 9/2002 | Bertrand et al. | |
| 6,514,767 B1 * | 2/2003 | Natan | 436/166 |
| 6,526,299 B2 | 2/2003 | Pickard | |
| 6,552,784 B1 | 4/2003 | Dietz et al. | |
| 6,590,204 B2 | 7/2003 | Baranov | |
| 6,603,537 B1 | 8/2003 | Dietz et al. | |
| 6,620,591 B1 | 9/2003 | Dunlay et al. | |
| 6,625,546 B2 | 9/2003 | Sepetov et al. | |
| 6,642,059 B2 | 11/2003 | Chait et al. | |
| 6,646,271 B2 | 11/2003 | Yokokawa et al. | |
| 6,687,395 B1 | 2/2004 | Dietz et al. | |
| 6,753,966 B2 | 6/2004 | Von Rosenberg | |
| 6,787,761 B2 | 9/2004 | Hastings | |
| 6,800,860 B2 | 10/2004 | Dietz et al. | |
| 6,835,927 B2 | 12/2004 | Becker et al. | |
| 6,858,435 B2 | 2/2005 | Chervet et al. | |
| 6,873,915 B2 | 3/2005 | Hastings | |
| 6,937,330 B2 | 8/2005 | Dietz et al. | |
| 6,950,185 B1 * | 9/2005 | Da Silva et al. | 356/326 |
| 6,962,818 B2 | 11/2005 | Schneider et al. | |
| 6,979,830 B2 | 12/2005 | Dietz et al. | |
| 2001/0019829 A1 | 9/2001 | Nelson et al. | |
| 2002/0049152 A1 | 4/2002 | Nock et al. | |
| 2002/0053545 A1 | 5/2002 | Greef | |
| 2002/0095419 A1 | 7/2002 | Parce | |
| 2002/0102610 A1 | 8/2002 | Townsend et al. | |
| 2002/0123055 A1 | 9/2002 | Estell et al. | |
| 2002/0141051 A1 * | 10/2002 | Vogt et al. | 359/385 |
| 2003/0087322 A9 | 5/2003 | Aebersold et al. | |
| 2004/0257576 A1 * | 12/2004 | Kirsch et al. | 356/436 |
| 2006/0000984 A1 * | 1/2006 | Wolleschensky et al. | 250/458.1 |

FOREIGN PATENT DOCUMENTS

| | | |
|---|---|---|
| EP | 0296136 | 12/1988 |
| EP | 0421736 | 4/1991 |
| EP | 0681177 | 11/1995 |
| EP | 0969283 | 1/2000 |
| GB | 1407247 | 9/1975 |
| JP | 11281478 A * | 10/1999 |
| SU | 1226077 A * | 4/1986 |
| WO | WO-97 43732 | 11/1997 |
| WO | WO-98 16661 | 4/1998 |
| WO | WO-00 67017 | 11/2000 |
| WO | WO-00 70340 | 11/2000 |
| WO | WO-01 35266 | 5/2001 |
| WO | WO-01 44269 | 6/2001 |

WO  WO 02/088819 A2 * 11/2002

OTHER PUBLICATIONS

Kantor, 2002, "Comprehensive Phenotyping and Biological Marker Discovery," *Dis Markers*,18(2):91-97.
Kantor et al., 2004, "Biomarker Discovery by Comprehensive Phenotyping for Autoimmune Diseases," *Clinical Immunology*, 111:186-195.
Walton et al., 2000, "Microvolume Laser Scanning Cytometry Platform for Biological Marker Discovery," *Proc.SPIE-Int.Soc.Opt. Eng.*, 3926:192-201.
Aach et al., 2001, "Aligning Gene Expression Time Series With Time Warping Algorithms", Bioinformatics 17:495-508.
Baumgarth et al., 2000, "A Practical Approach to Multicolor Flow Cytometry for Immunophenotyping," J. Immunol Methods, 243(1-2):77-97.
Beavis et al., 1996, "Alio-7: A New Fluorescent Tandem Dye for Use in Flow Cytometry," Cytometry 24(4):390-395.
Berlier et al., 2003, "Quantitative Comparison of Long-Wavelength Alexa Fluor Dyes to Cy Dyes: Fluorescence of the Dyes and Their Bioconjugates," J. Histochem Cytochem, 51(12):1699-1712.
Beu et al., 2004, "Broadband Phase Correction of FT-ICR Mass Spectra via Simultaneous Excitation and Detection," Anal. Chem., v. 76, pp. 5756-5761.
Breen et al., 2000, "Automatic Poisson Peak Harvesting for High Throughput Protein Identification", Electrophoresis, 21:2243-2251.
Bruchez et al., 1998, "Semiconductor Nanocrystals as Fluorescent Biological Labels," Science, 281(5385):2013-2016.
Bryant et al., 2001, "Principal Component Analysis of Mass Spectra of Peptides Generated from the Tryptic Digestion of Protein Mixtures," Rapid Commun. Mass Spectrum. 15:418-427.
Bucknall et al., 2002, "Practical Quantitative Biomedical Applications of MALDI-TOF Mass Spectrometry", J. Am. Soc. Mass Spectrom. 13:1015.
Bylund, 2001, "Chemometric Tools for Enhanced Performance in Liquid Chromatography—Mass Spectrometry," Acta Univ. Ups., Comprehensive Summaries of Uppsala Dissertations from the Faculty of Science and Technology, 07. 47 pp. Uppsala. ISBN 91-554-4946-8.
Bylund et al.,2002, "Chromatographic Alignment by Warping and Dynamic Programming as a Pre-Processing Tool for PARAFAC Modelling of Liquid Chromatography-Mass Spectrometry Data". J. or Chromatography A., 961:237-244.
Cagney et al., 2002, "De Novo Peptide Sequencing and Quantitative Profiling of Complex Protein Mixtures Using Mass-Coded Abundance Tagging", Nat. Biotech. 20:163.
Caprioli et al., 1972, "Use of Stable Isotopes", Biochem. Appl. Mass Spectrom. 27:735.
Chace, 2001, "Mass Spectrometry in the Clinical Laboratory", Chem. Rev. 101: 445-477.
Chelius et al., 2002, "Quantitative Profiling of Proteins in Complex Mixtures Using Liquid Chromatography and Mass Spectrometry", J. Proteome Res. 1:317-323.
Coons, 1961, "The Beginnings of Immunofluorescence," J. Immunol, 87:499-503.
De Rosa et al., 2001, "11-Color, 13-Parameter Flow Cytometry: Identification of Human Naive T-Cells by Phenotype, Function, and T-cell Receptor Diversity," Nat. Med., 7(2):245-248.
De Rosa et al., 2003, "Beyond Six Colors: a New Era in Flow Cytometry," Nature Medicine, vol. 9, No. 1, pp. 112-117.
Dietz et al., 1996, "Volumetric Capillary Cytometry: A New Method for Absolute Cell Enumeration", Cytometry 23:177-186.
do Lago et al., 1995, "Applying Moving Median Digital Filter to Mass Spectrometry and Potentiometric Titration", Anal. Chim. Acta, 310: 281-288.
Elavathil et al., 1996, "Reproducibility of DNA Ploidy and S-Phase Values from Parraffin-Embedded Tissue", Analytical and Quantitative Cytology and Histology, vol. 18, No. 4, 316-322.
Felinger, 1998, "Data Analysis and Signal Processing in Chromatography," Data Handling in Science and Technology, vol. 21,pp. 149-152.

Fiehn et al., 2000, "Metabolite Profiling for Plant Functional Genomics", Nat. Biotech. 18:1157-1161.
Glazer et al., 1983, "Fluorescent Tandem Phycobiliprotein Conjugates- Emission Wavelength Shifting by Energy Transfer," Biophys J, 43(3):383-386.
Grung et al., 1995, "Retention Time Shift Adjustments of Two-Way Chromatograms Using Bessel's Inequality", Analytica Chimica Acta, 304:57-66.
Gygi et al.,1999, "Quantitative Analysis of Complex Protein Mixtures Using Isotope-Coded Affinity Tabs", Nat. Biotech., 17:994-999.
Ha et al., 1999, "Single-molecule Fluorescence Spectroscopy of Enzyme Conformational Dynamics and Cleavage Mechanism," Biophysics, vol. 96, pp. 893-898.
Hamberg et al.,1973, "Quanitative Studies on Prostaglandin Synthesis in Man", Anal. Biochem., 55:368.
Hastings et al., 2002, "New Algorithms for Processing and Peak Detection in Liquid Chromatography/Mass Spectrometry Data", Rapid Communications in Mass Spectrometry, 16(5):462-465,467.
Holst, 1998, "CCD Arrays, Camera and Displays", 2d Ed., JCD Publishing and SPIE Optical Engineering Press, pp. i-xxiii.
Jeanmaire et al., 1977, "Surface Raman Spectroelectrochemistry Part 1: Heterocyclic, Aromatic, and Allphatic Amines Adsorbed on the Anodized Silver Electrode," J. Electroanal. Chem., 84:1-20.
Ji et al., 2000, "Strategy for Qualitative and Quantitative Analysis in Proteomics Based on Signature Peptides", J. Chromat. B 745:197.
Kamentsky, 2001, "Laser Scanning Cytometry," Methods Cell. Biol., 63:51-87.
Kassidas et al., 1998, "Synchronization of Batch Trajectories Using Dynamic Time Warping", AlChE Journal 44(4):864-875.
Kast et al., 2003, "Noise Filtering Techniques for Electrospray Quadrupole Time of Fluid Mass Spectra," J. Am. Soc. Mass Spectrom., v. 14, pp. 766-776.
Koradi et al., 1998, "Automated Peak Picking and Peak Integration in Macromolecular NMR Spectra Using AUTOPSY", J. Magn. Reson., 135:288-297.
Mahallngam, 1996, "Analysis of Surface Density of Expression of Molecules by Flow Cytometry", Cytometry 24:190.
Moore et al., 1993, "Median Filitering for Removal of Low-Frequency Background Drift," Anal.Chem., 65: 188-191.
Mujumdar et al., 1996, "Cyanine-Labelling Reagents: Sulfoindocyanine Succinimidyl Esters," Bioconjug Chem, 7, 356-362.
Nelson et al., 1995, "Mass Spectrometric Immunoassay", Anal. Chem. 67:1153.
Nielsen et al., 1998, "Aligning of Single and Multiple Wavelength Chromatographic Profiles for Chemometric Data Analysis Using Correlation Optimised Warping", J. of Chromatography A. 805:17-35.
Norton et al., 2000, "Cell Enumeration and Characterization in Microvolume Laser Scanning Cytometry: A Multicolor Image Processing Package," IBOS Society of Photo-Optical Instrumentation Engineers, p. 20-30.
Oda et al., 1999, "Accurate Quantitation of Protein Expression and Site-Specific Phosphorylation", Proc. Natl. Acad. Sci. USA 96:6591.
Oi et al., 1982, "Fluorescent Phycobiliprotein Conjugates for Analyses of Cells and Molecules," J. Cell Biol, 93(3):981-6.
Panchuk-Voloshina et al., 1999, "Alexa Dyes, A Series of New Fluorescent Dyes That Yield Exceptionally Bright, Photostable Conjugates," J. Histochem Cytochem, 47(9):1179-88.
Perez et al., 2002, "Simultaneous Measurement of Multiple Active Kinase States Using Polychromatic Flow Cytometry," Nat Biotechnol. 20(2):155-162.
Perez et al., 2004, "Flow Cytometric Analysis of Kinase Signaling Cascades," Methods Mol Biol, 263:67-94.
Perou et al., 2000, "Molecular Portraits of Human Breast Tumours", Nature, vol. 406, pp. 747-752.
Pinajian et al., 1953, "The Isotope Dilution Procedure of Analysis", J. Am. Phar, Assoc., 301-304.
Pravdova et al., 2002, "A Comparison of Two Algorithms for Warping of Analytical Signals", Analytica Chimica Acta 456:77-92.

Prazen et al., Jan. 15, 1998, "Standardization of Second-Order Chromatographic/Spectroscopic Data for Optimum Chemical Analysis", Anal. Chem. 70:218-225.

Proceedings of SPIE V, 1997, "Ultrasensitive Biochemical Diagnostics II", The International Society for Optical Engineering, Feb. 10-12, San Jose, CA.

Roederer et al., 1996, "Cy7PE and Cy7APC: Bright New Probes for Immunofluorescence," Cytometry, 24(3):191-7.

Sakoe et al., 2002, "Dynamic Programming Algorithm Optimization for Spoken Word Recognition" IEEE Transactions on Acoustics, Speech and Signal Processing ASSP26(1):43-49.

Schoonjans et al., 2000, "Use of Mass Spectrometry for Assessing Similarity/Diversity of Natural Products with Unknown Chemical Structures", J. Pharm. & Biomed. Analysis, 21:1197-1214.

Stein, 1999, "An Integrated Method for Spectrum Extraction and Compound Identification from Gas Chromatography/Mass Spectrometry Data", J Am Soc Mass Spectrum 10:770-781.

Stewart et al., 1999, "Four Color Compensation", Cytometry, vol. 38, No. 4, 161-175.

Van Duyne, 1979, "Laser Excitation of Raman Scattering from Adsorbed Molecules on Electrode Surfaces," In: Moore CD, editor, Chemical and Biochemical Applications of Lasers, pp. 101-185.

Voyksner et al., 1999, "Investigating the use of an Octupole Ion Guide for Ion Storage and High-pass Mass Filtering to Improve the Quatitative Performance of Electro spray Ion Trap Mass Spectrometry," Rapid Commun. Mass Spectrom., v. 13, pp. 1427-1437.

Waggoner et al., 1993, "PE-CY5- A New Fluorescent Antibody Label for Three-color Flow Cytometry with a Single Laser," Ann N Y Acad Sci, 677:185-93.

Wang et al.,1987, "Time-Warping Algorithm Applied to Chromatographic Peak Matching Gas Chromatography/Fourier Transform Infrared/Mass Spectrometry", Analytical Chemistry 59:649-654.

Wang et al., 2003, "Quantification of Proteins and Metabolites by Mass Spectrometry Without Isotopic Labeling or Spiked Standards", Anal. Chem. 75:4818.

Watson et al., 2003, "Lighting up Cells with Quantum Dots," Biotechniques, 34(2):296-300, 302-3.

Windig et al., 1996, "A Noise and Background Reduction Method for Component Detection in Liquid Chromatography/Mass Spectrometry", Anal. Chem., 68: 3602-3606.

Wu et al., 2003, "Immunofluorescent Labelling of Cancer Marker Her2 and Other Cellular Targets with Semiconductor Quantum Dots," Nat Biotechnol, 21(1):41-6.

Zuck et al., 1999, "Ligand-receptor Binding Measured by Laser-scanning Imaging," Proc. Natl. Acad. Sci., 96(20):11122-11127.

Constantino, et al., 2001 "Single-Molecule Detection Using Surface-Enhanced Resonance Raman Scattering and Langmuir-Blodgett Monolayers," Anal. Chem., vol. 73, pp. 3674-3678.

Doering et al., 2002, "Single-Molecule and Single-Nanoparticle SERS: Examining the Roles of Surface Active Sites and Chemical Enhancement," *J. Phys. Chem. B.*, 106:311-317.

Ha, T., 2001, "Single-Molecule Fluorescence Resonance Energy Transfer," *Methods*, 25:78-86.

Kneipp et al., 1997, "Single Molecule Detection Using Surface-Enhanced Raman Scattering (SERS)," *Physical Review Letters*, 78(9):1667-1670.

Kneipp et al., 1999, "Ultrasensitive Chemical Analysis by Raman Spectroscopy," *Chem. Rev.*, 99:2957-2975.

Martens et al., 1999, "A Generic Particle-Based Nonradioactive Homogeneous Multiplex Method for High-Throughput Screening Using Microvolume Fluorimetry," *Analytical Biochemistry*, 273:20-31.

Mulvaney, et al., 2000 "Raman Spectroscopy," Proc. Anal. Chem., vol. 72, pp. 145R-157R.

Mulvaney et al., 2003, "Glass-Coated, Analyte-Tagged Nanoparticles: A New Tagging System Based on Detection with Surface-Enhanced Raman Scattering," *Langmuir*, 19:4784-4790.

Nie et al., 1997, "Probing Single Molecules and Single Nanoparticles by Surface-Enhanced Raman Scattering," *Science*, New Series, 275(5303):1102-1106.

Rossetti et al., 1982, "Electron-Hole Recombination Emission as a Probe of Surface Chemistry in Aqueous CdS Colloids," *J. Phys. Chem.*, 86:4470-4472.

Steigerwald et al., 1988, "Surface Derivatization and Isolation of Semiconductor Cluster Molecules," *J. Am. Chem. Soc.*, 110:3046-3050.

Swartzman et al., 1999, "A Homogeneous and Multiplexed Immunoassay for High-Throughput Screening Using Fluorometric Microvolume Assay Technology," *Analytical Biochemistry*, 271:143-151.

Tibbe et al., 1999, "Optical Tracking and Detection of Immunomagnetically Selected and Aligned Cells," *Nature Biotechnology*, 17:1210-1213.

Wyant et al., 2001, "Whole Blood Microvolume Laser Scanning Cytometry for Monitoring Resting and Activated Platelets," *Platelets*, 12:309-318.

\* cited by examiner

POLYCHRONIC LASER SCANNING SYSTEM AND METHOD OF USE

CROSS REFERENCE TO RELATED APPLICATION

The present application claims the benefit under 35 U.S.C. §119(e) of U.S. Provisional Application No. 60/559,322 filed on Apr. 2, 2004, the entire disclosure of which is incorporated herein by reference in its entirety.

STATEMENT REGARDING FEDERALLY SPONSORED RESEARCH OR DEVELOPMENT

This invention was made with United States Government support under Cooperative Agreement No. 70NANB0H3000 awarded by the National Institute of Standards and Technology (NIST). The United States Government has certain rights in the invention.

FIELD OF THE INVENTION

The present invention relates to a novel laser scanning system for monitoring particles, such as cells, in a liquid suspension, such as whole blood. Among other things, the present invention provides spectral flexibility and compatibility with a large number of both light emitting molecules and newly developed surface enhanced Raman scattering (SERS) tags.

BACKGROUND OF THE INVENTION

White blood cells and their secreted products are key elements of immune systems biology and important indicators of patient health and disease. Large numbers of such variables in whole blood and other cell suspensions, including cell populations, cell surface antigens and intracellular molecules may be immunoprofiled using the microvolume laser scanning cytometry (MLSC) system. Immunoprofiling of cells and molecules, and use of a MLSC system are described in Kantor et al., 2004, "Immune Systems Biology: Immunoprofiling of Cells and Molecules," *Biotechniques*, 36(3):520-4; in Walton et al., 2000, "Microvolume Laser Scanning Cytometry Platform for Biological Marker Discovery," *Proc. SPIE-Int. Soc. Opt. Eng.*, 3926:192-201; and in Kantor et al., 2004, "Biomarker Discovery by Comprehensive Phenotyping for Autoimmune Diseases," *Clinical Immunology*, 111:186-195, all of which are incorporated herein by reference in their entirety. In addition, the MLSC and related optical cuvette are described in Dietz et al., "System for MicrovolumeLaser Scanning Cytometry," U.S. Pat. No. 6,687,395 (Feb. 3, 2004); Dietz et al., "Optical architectures for Microvolume Laser-Scanning Cytometers," U.S. Pat. No. 6,603,537 (Aug. 5, 2003); and Dietz et al., "Disposable Optical Cuvette Cartridge," U.S. Pat. No. 6,552,784 (Apr. 22, 2003), all incorporated herein by reference in their entirety. The above noted MLSC system of U.S. Pat. No. 6,687,395 incorporates photomultiplier tubes (PMTs) and is optimized for analysis of whole blood, but is limited to three or four color assays because of the limitations of traditional fluorophores and static detection channels of the PMT based detection system.

Prior laser scanning cytometers and flow cytometers depend on the arrangement of dichroic filters to define detection channels with each requiring a dedicated photomultiplier tube. The throughput and sensitivity of these systems is mostly limited by low detector efficiencies (less than 15%), especially in the red region of the spectrum that is used for whole blood assays. Accordingly, there is an unmet need for a polychromatic laser scanning cytometry system with a high level of multiplexing that can be used in clinical studies. Such technology is critical for identifying fine subsets of cells within the extremely complex immune system and relating them to disease pathogenesis.

In MLSC, as in flow cytometry, fluorophore-tagged antibody reagents specific for cellular antigens are used to identify, characterize, and enumerate specific leukocyte populations. In order to operate with whole blood and minimize the effects of auto-fluorescence and light attenuation, fluorophores are used that can be excited in the red and near infrared region (>600 nm) of the spectrum. APC, Cy5, Cy5.5, Cy7APC and some of the Alexa dyes work well in the system. See Mujumdar et al., 1993, "Cyanine Dye Labeling Reagents: Sulfoindocyanine Succinimidyl Esters," *Bioconjug Chem*, 4(2):105-11; Roederer et al., 1996, "Cy7PE and Cy7APC: Bright New Probes for Immunofluorescence," *Cytometry*, 24(3):191-7; Beavis et al., "Allo-7: A New Fluorescent Tandem Dye for Use in Flow Cytometry, "24(4):390-395; Panchuk-Voloshina et al., 1999, "Alexa Dyes, A Series of New Fluorescent Dyes That Yield Exceptionally Bright, Photostable Conjugates," *J. Histochem Cytochem*, 47(9):1179-88; and Berlier et al., 2003, "Quantitative Comparison of Long-Wavelength Alexa Fluor Dyes to Cy Dyes: Fluorescence of the Dyes and Their Bioconjugates," *J. Histochem Cytochem*, 51(12):1699-712, all of which are incorporated herein by reference in their entirety.

In contrast to flow cytometry, in a MLSC system the laser scans over stationary cells rather than cells flowing past the laser. A laser beam with a focused spot size appropriate for the imaging of targeted cells and particles is scanned across the sample in one direction while the sample is translated relative to the optical system in a second orthogonal direction. By scanning a predetermined volume for each sample, such as by using a capillary, absolute cell counts (cells per microliter) are obtained directly. In this respect the system is similar to hematology analyzers and different from other laser scanning systems that focus on high throughput screening cell morphology or rare cell applications. See Groner et al., 1995, "Practical Guide to Modern Hematology Analyzers," Chichester, England: John Wiley and Sons,"; Zuck et al., 1999, "Ligand-receptor Binding Measured by Laser-scanning Imaging," *Proc. Natl. Acad. Sci.*, 96(20):11122-11127; Martens et al., 1999, "A Generic Particle-based Nonradioactive Homogeneous Multiplex Method for High-throughput Screening Using Microvolume Fluorimetry," *Anal. Biochem*, 273(1):20-31; Swartzman et al., 1999, "A Homogeneous and Multiplexed Immunoassay for High-throughput Screening Using Fluorometric Microvolume Assay Technology," *Anal. Biochem.*, 271(2):143-151; Kamentsky, 2001 "Laser Scanning Cytometry," *Methods Cell. Biol.*, 63:51-87; and Tibbe et al., 1999, "Optical Tracking and Detection of Immunomagnetically Selected and Aligned Cells," *Nat. Biotechnol.*, 17(12):1210-1213, all of which are incorporated herein by reference in their entirety. In general, a MLSC system is designed for the performance of many different assays on a large number of patient samples. A comparison between the capabilities of a a MLSC system and flow cytometry is provided in Table 1. Although the scanning times per individual assay are similar, a MLSC system is much more efficient than a flow cytometry system with respect to sample preparation and data analysis. Sample handling and operator interaction are minimized. There is no need to prepare peripheral blood mononuclear cells (PBMC) by density gradients or to wash away unreacted reagent. In terms of processing and absolute cell counts, significant advantages are provided by a MLSC system for whole blood and, to a lesser extent, erythrocyte lysed blood preparations. Informatics tools facilitate automated collection, processing and analysis of the data. This data pipelining approach speeds data flow and reduces user error.

Traditionally, cytometry instruments such as flow-cytometers or MLSC system instruments used photomultiplier tubes (PMT) for the detection of the fluorescence signals. Advantages of PMTs are a large dynamic range and a high bandwidth, allowing for data rates of several hundred kHz. However, PMTs require high voltage power supplies, have low quantum efficiency (especially for the red and infrared) and, because they are basically vacuum tubes, PMTs are inherently mechanically instable. In spite of these significant disadvantages, PMTs have been the fluorescence detector of choice in cytometry for a long time. Typically, the emitted fluorescence is split into a number of separate color channels using dichroic beamsplitters and each channel comes equipped with a dedicated PMT. The number of detection channels is limited by the availability of appropriate dichroic mirrors and is fixed for a given instrument. Due to the optical properties of dichroic beam splitters, the color channels have to have a minimum spectral width, significantly limiting the number of detection channels that can be defined in the range between 650 and 800 nm.

With regard to the general background of CCDs, the basic principle of solid-state CCDs is the photovoltaic effect; that is, photons impacting into a silicon layer create electron-hole pairs. Arrays of surface electrodes are used to keep the charge confined to small rectangular areas called pixels. By manipulating the electrode potentials, the charge can be moved from pixel to pixel towards a charge-sensing node where it ultimately is converted into a digital number using an A/D-converter. CCDs offer the advantages of avoiding high voltage power requirements of PMTs and have higher quantum efficiency than PMT systems. In addition, CCDs are more stable because of their solid-state construction.

There is an ever increasing number of available antibodies to cell surface antigens (e.g., there are more than 200 CD antigens) and intracellular components. In addition, available techniques include analysis of phosphorylated molecules. See Perez et al., 2002, "Simultaneous Measurement of Multiple Active Kinase States Using Polychromatic Flow Cytometry," *Nat Biotechnol*, 20(2):155-162; and Perez et al., 2004, "Flow Cytometric Analysis of Kinase Signaling Cascades," *Methods Mol Biol*, 263:67-94, both of which are incorporated herein by reference in their entirety. This has driven the highly detailed subsetting of cell populations and inclusion of more and more colors in cytometric analysis. See De Rosa et al., 2003, "Beyond Six Colors: A New Era In Flow Cytometry," *Nat. Med.*, 9(1):112-117.

Flow cytometry based systems detecting eight or more tags require multiple laser excitations and are not optimized for whole blood applications and absolute cell counting. Multiple tags using multiple laser excitations are described in Roederer et al., 1997, "8 Color, 10-parameter Flow Cytometry to Elucidate Complex Leukocyte Heterogeneity," *Cytometry*, 29(4):328-39; Baumgarth et al., 2000, "A Practical Approach to Multicolor Flow Cytometry for Immunophenotyping," *J. Immunol Methods*, 243(1-2):77-97; and De Rosa et al., 2001, "11-Color, 13-Parameter Flow Cytometry: Identification of Human Naive T-Cells by Phenotype, Function, and T-cell Receptor Diversity," *Nat. Med.*, 7(2):245-248, all of which are incorporated herein by reference in their entirety.

The staining reaction for an MLSC sample can be done in whole blood or other single cell suspensions. Peripheral blood mononuclear cells, erythrocyte-lysed blood, synovial fluid, bronchioalveolar lavage, splenocytes, and cell lines have been used in a MLSC system, as have viably frozen and thawed cells. In general, assays can be conducted in homogeneous mode. There is no need to wash the reagent away; quantitative dilution of the blood-antibody mixture is usually sufficient sample preparation. Addition of permeabilization and washing steps enable the monitoring of intracellular antigens. Each capillary array holds 32 separate assays and is compatible with multi-channel pipetting devices. The cell-antibody mixtures are loaded into the capillaries and scanned.

Reporter tags are needed in cellular assays to identify specific components from among the thousands of molecules present in a cell or biological sample. A reporter tag consists of at least two components. The reactive component of the tag is capable of undergoing a highly selective and sensitive reaction with the functional group of interest. Examples of reactive tag components are antibodies specific to the antigen of interest. The second element of the reporter tag is an optically active component, which can absorb energy in the form of photons at one wavelength and release energy in the form of photons with wavelengths different from the excitation wavelength. Examples for optically active components of a reporter tag are organic fluorophores, fluorescent proteins, Quantum Dot crystals and SERS particles. Reporter tags are expected to be thermodynamically stable, compatible with the samples of interest, give a quantitative response proportional to the concentration of the functional group of interest, and must be suitable for multiplexing with other tags. Most suitable for the scanner of the present invention are tags compatible with whole blood samples and optical characteristics that allow for using six or more tags simultaneously with only a single laser source.

As described in by Coons, 1961, "The Beginnings of Immunofluorescence," *J. Immunol*, 87:499-503, incorporated herein by reference in its entirety, organic fluorescence labels became popular in the 1950's, with a review of fluorescence labeling of tissue appearing in 1961. Organic dyes, along with fluorescent proteins and tandem dyes are the principal tags used in cytometry today. See Oi et al., 1982, "Fluorescent Phycobiliprotein Conjugates for Analyses of Cells and Molecules," *J. Cell Biol*, 93(3):981-6; Glazer et al., 1983, "Fluorescent Tandem Phycobiliprotein Conjugates-Emission Wavelength Shifting by Energy Transfer," *Biophys J*, 43(3):383-6; and Waggoner et al., 1993, "PE-CY5—A New Fluorescent Antibody Label for Three-color Flow Cytometry with a Single Laser," *Ann N Y Acad Sci*, 677:185-93, all of which are incorporated herein by reference in their entirety. Fluorescence detection is very sensitive, as has been demonstrated by the ability to detect single molecules as described in Ha, 2001, "Single-molecule Fluorescence Resonance Energy Transfer," *Methods*, 25(1): 78-86 (incorporated herein by reference in its entirety), and signals generated by the tag are proportional to the number of tag molecules interrogated, making it a quantitative technique. Limitations include susceptibility to photobleaching, the limited number of spectrally distinct dyes especially above 600 nm, broad emission spectra, typically 50-100 nm and the small Stoke shift for organic and protein dyes. Thus with a single laser excitation, low levels of multiplexing are possible for organic fluorophores by selecting dyes with different emission wavelengths. Ideally the emission profiles are non-overlapping, as it is difficult to accurately measure a low concentration of one dye in the presence of a large concentration of a second dye, when the profiles overlap. In addition, when dyes are chosen with well-separated emission spectra, the excitation spectra also generally become separated, such that a single excitation wavelength can no longer be used. This can be overcome in part with the preparation of tandem dyes that use energy transfer to extend the effective Stokes shift from excitation to emission. It is apparent however, that simultaneous quantitative detection using organic fluorophores and a single laser excitation is limited to a small number of tags (e.g., 3-5) with emission greater than 600 nm needed for whole blood assays.

In recent years there has been an increase in the use of nanoparticles as biological tags. The driving force behind this development has been the desire to eliminate the use of organic labeling, which have shortcomings, as described above. Much of this work has been in the development of quantum dots (also referred to herein as "Qdots"). Quantum dots take advantage of the quantum confinement effect, giving the nanoparticles unique optical properties. Quantum dots offer advantages over organic dye molecules in that they have brighter emission, significantly narrower emission spectra, and lack the characteristic spectral tail of organic dyes. See Steigerwald et al., 1988 "Surface Derivatization and Isolation of Semiconductor Cluster Molecules," *J. Am. Chem. Soc.,* 110:3046-3050; and Rosetti et al., 1982, "Electron-Hole Recombination Emission as a Probe of Surface Chemistry in Aqueous Cds Colloids," *J. Phys. Chem.,* 86:4470-4472, both of which are incorporated herein by reference in their entirety. The average emission spectrum of currently commercially available quantum dots is typically 30-50 nm wide and potentially allows higher levels of multiplexing than with traditional fluorophores. Other key advantages of Qdots for cytometry applications include significantly decreased photobleaching and relatively large Stokes shifts, which enable emissions over a large wavelengths region using a single excitation source. Due to these advantages, quantum dots have begun to be used in a number of real-world biological applications including cellular assays. See Watson et al., 2003, "Lighting up Cells with Quantum Dots," *Biotechniques,* 34(2):296-300, 302-3; Wu et al., 2003, "Immunofluorescent Labeling of Cancer Marker Her2 and Other Cellular Targets with Semiconductor Quantum Dots," *Nat Biotechnol,* 21(1):41-6; and Bruchez et al., 1998, "Semiconductor Nanocrystals as Fluorescent Biological Labels," *Science,* 281(5385):2013-6, all of which are incorporated herein by reference in their entirety. Limitations include the small set of currently available colors, especially in the red and infrared. There are currently two such commercially available tags (Quantum Dot Corp., Hayward, Calif.) with emissions at 655 and 705 nm and it is expected that the set will continue to be expanded. The unique emission lifetime characteristics make Qdots best suited for longer integration times. Over all, simultaneous quantitative detection using Qdots and a single laser excitation has long-term potential for 6 to 10 tags with emission greater than 600, and up to 20 tags with emission greater than 400 nm.

Raman spectroscopy is an optical technique in which the measurement of scattered light is used to identify molecular vibrations and hence elucidate the structure of molecules. While the much more common infrared (IR) spectroscopy also uses the fingerprinting ability of vibrational spectroscopy to identify organic molecules, optical detection in the infrared region does not work well for biological analysis because of the presence of water in biological samples. The extremely dipolar water molecule has strong absorption bands in the IR-region, which would interfere with any signal of the bio-molecule in this region. Raman scattering, however, can be observed in the visible and near-infrared regions, where the absorption of water is much lower. In addition, water by itself is also a weak Raman-scatterer. Thus, even though its concentration in biological samples is orders of magnitudes higher than the molecule of interest, water does not interfere with the Raman signature of the low-concentration tag.

However, Raman scattering is a rare event, and measurements typically have poor sensitivity. Surface enhanced Raman scattering (SERS) was a phenomenon first reported in the 1970's, in which Raman scattering from roughened metal surfaces was found to increase by as much as 106 fold (32, 33). See Van Duyne, 1979, "Laser Excitation of Raman Scattering from Adsorbed Molecules on Electrode Surfaces," In: Moore C B, editor, Chemical and Biochemical Applications of Lasers, p 101-185; Jeanmaire et al., 1977, "Surface Raman Spectroelectrochemistry Part 1: Heterocyclic, Aromatic, and Aliphatic Amines Adsorbed on the Anodized Silver Electrode," *J. Electroanal. Chem.,* 84:1-20, both of which are incorporated herein by reference in their entirety. Steady progress was made towards an understanding of the SERS effect through the following decades. See Kneipp et al., 1999, "Ultrasensitive Chemical Analysis by Raman Spectroscopy," *Chem. Rev.,* 99:2957-2975; and Mulvaney et al., 2000, "Raman Spectroscopy," *Anal. Chem.,* 145R-157R, both of which are incorporated herein by reference in their entirety. In 1997, Nie and Emory, followed by Kneipp et al. first reported single molecule detection using SERS. See Nie et al., 1997, "Probing Single Molecules and Single nanoparticles by Surface-Enhanced Raman Scattering," *Science,* 275:1102-1106; and Kneipp et al., 1997 "Single-Molecule Detection Using Surface-Enhanced Raman Scattering (SERS)," *Phys. Rev. Lett.,* 1667-1670, both of which are incorporated herein by reference in their entirety. Since then numerous reports have verified that SERS is capable of single molecule detection. See Doering et al., 2002, "Single-molecule and Single-nanoparticle Sers: Examining the Roles of Surface Active Sites and Chemical Enhancement," *J. Phys. Chem.,* 311-317; Constantino et al., 2001, "Single-molecule Detection Using Surface-enhanced Resonance Raman Scattering and Langmuir-blodgett Monolayers," *Anal. Chem.,* 73:3674-3678; and Bizzarri et al., 2002, "Surface-enhanced Resonance Raman Spectroscopy Signals from Single Myoglobin Molecules," *Appl. Spectrosc,* 56:1531-1537, all of which are incorporated herein by reference in their entirety.

Importantly, these measurements indicate an enhancement factor of up to 1014 for single molecules. These results make SERS a candidate technique when measurements with high sensitivity and high multiplexing are required. Of course, single-molecule detection sensitivity is not required for typical cytometry applications. Glass-encapsulated SERS tags were recently reported (44) by Mulvaney et al., 2003, "Glass-coated, Analyte-tagged Nanoparticles: A New Tagging System Based on Detection with Surface-enhanced Raman Scattering," *Langmuir,* 19:4784-4790. See also, Natan, "Surface enhanced spectroscopy-active composite nanoparticles" U.S. Pat. No. 6,514,767 (Feb. 4, 2003), incorporated herein by reference in its entirety. Raman scattering is confined to a relative small spectral window around the excitation wavelength. Raman spectra usually are reported using wavenumber units [$cm^{-1}$]. A typical Raman spectrum extends between 200 $cm^{-1}$ and 3800 $cm^{-1}$ from the excitation wavelength, with individual spectral features covering 20 cm$^{-1}$ to 50 cm$^{-1}$. Based on these parameters, a Raman spectrum can exhibit up to 150 distinguishable spectral features. Since it is possible to design particles with specific Raman signatures, the number of distinguishable Raman tags excitable with a single laser source greatly exceeds the number of available fluorescent tags. If a Helium-Neon laser is used for excitation, a 20 cm$^{-1}$-wide Raman-feature corresponds to a spectral bandpass of approximately 1 nm only. Because of these extremely fine spectral features, only instruments with a large number of detection channels or with freely configurable bandpass definition of the detection channels can truly take advantage of the multiplexing capabilities of Raman tags. Both characteristics are implemented in the claimed polychromatic laser-scanning instrument with CCD detection.

Unlike fluorescent tags, Raman tags do not need to gain enough energy to populate an electronically excited state. Thus, photobleaching of the tags is greatly reduced in Raman when compared to fluorophores.

SUMMARY OF THE INVENTION

The present invention comprises a laser scanner that provides spectral flexibility needed for the spectroscopic monitoring of highly multiplexed cellular and particle assays in whole blood or other suspensions. Thus, in accordance with embodiments of the present invnetion, a system for performing laser scanning of a liquid sample containing particles is provided, the system comprising a means for scanning an excitation laser beam from an excitation laser across the sample, a means for focusing the excitation laser beam into the sample, a means for collecting a light emitted from the sample and its constituents in response to the excitation laser beam, a means for de-scanning the collected emission light, a means for spectrally dispersing the collected emission light, a means for imaging the spectrally dispersed emission light as a spectrum, and a means for detecting the spectrum in one or more detection channels simultaneously according to its wavelength using a two-dimensional detector surface. In addition, the system may further comprise a means for changing a readout pattern of the two-dimensional detector surface in real-time, wherein the means for changing effectively reformats (a) a number of simultaneous detection channels, and (b) a spectral bandpass of at least one of the one or more detection channels.

In accordance with various embodiments of the invention, the two-dimensional detector surface comprises a charge coupled device or a CMOS sensor.

In accordance with embodiments of the present invention, the means for scanning (or the scanner) may comprise raster scanning. For example, a galvanometer-mirror may be used to implement one axis of the raster-scan across a surface of the sample, and a second axis of the raster scan may be implemented by using a linear translation stage. Alternatively, a first galvanometer-mirror may be used to implement one axis of the raster-scan across a surface of the sample, and a second galvanometer-mirror may be used to implement a second axis of the raster scan. In accordance with embodiments of the present invention, the means for scanning and the means for de-scanning comprise a single (or common) galvanometer-mirror.

Various embodiments of the present invention may be used to scan one or more samples, wherein the one or more samples comprise suspensions of cells, man-made particles, and mixtures thereof. Structures used to hold the one or more samples may comprise one or more capillaries having a known volume, one or more non-capillary containers comprising well plates, or one or more slides comprising a flat surface.

In accoradnce with embodiments of the present invention, the means for focusing and the means for collecting comprise a common objective, wherein the common objective focuses the excitation laser into the sample and confocally collects the light emitted in response to the delivered excitation laser beam. In addition, in accordance with various embodiments of the present invention, the common objective comprises an F-Theta scan lens. For various embodiments of the present invention, an F-Theta scan lens may be used to focus the excitation laser beam or source into the sample and confocally collect the light emitted in response to the delivered excitation laser or source. In accordance with at least one embodiment of the present invention, the F-Theta scan lens comprises a focal length of about 6.8 mm, a numerical aperture of about 0.55, and a magnification of about 20.

In accordance with various embodiments of the present invention, the means for collecting, the means for spectrally dispersing, and the means for imaging provide a magnification appropriate to image the scanned particles onto the two-dimensional detector surface.

In accordance with embodiments of the present invention, the scanning system or apparatus comprises at least one afocal lens pair in a beam path of the collected emission light between a dichroic mirror and the means for spectrally dispersing or the spectrograph. In addition, various embodiments of the present invention comprise a pinhole at an internal focal plane of an afocal lens pair, wherein the pinhole prevents a substantial portion of light emitted from outside the focal plane of the excitation laser beam from reaching the means for spectrally dispersing (or the spectrograph).

In accordance with various embodiments of the present invention, the means for spectrally dispersing and the means for imaging comprise a concave holographic grating, or two toroidal mirrors and a planar diffraction grating.

In accordance with various embodiments of the present invention, the means for spectrally dispersing or spectrograph is adapted for a spectral range of 200 nm or more beginning from a wavelength of the excitation laser beam or excitation source and continuing to longer wavelengths.

In accordance with various embodiments of the present invention, a readout pattern of the two-dimensional detector surface can be changed in real-time by reprogramming one or more clock-drivers associated with the two-dimensional detector surface.

In accordance with various embodiments of the present invention, the two-dimensional detector surface is positioned in a focal plane of the means for imaging or the spectrograph such that a dispersion direction is preferably oriented substantially parallel to readout registers and shift registers of the two-dimensional detector surface, wherein the two-dimensional detector surface is selected from the group consisting of a charge coupled device and a CMOS sensor.

In accordance with embodiments of the present invention, except for the spectrum of the collected emission light emitted by the sample in response to the excitation laser beam or source, the two-dimensional detector surface is shielded from substantially all light.

In accordance with various embodiments of the present invention, the sample comprises one or more reporter tags, the one or more reporter tags comprising at least one reactive component associated with one or more functional groups of interest of at least one of the particles in the sample, and at least one optically active component for absorbing photons with a wavelength of the excitation laser and emitting photons at a different wavelength. In addition, for various embodiments of the invention, the at least one reactive component of the reporter tag is selected from the group consisting of an antibody, antigen, receptor, hapten, and lectin, and the at least one optically active component of the report tag is selected from the group consisting of an organic dye, a surface enhanced Raman scattering particle, a quantum dot, an up-converting phosphor, a fluorescent protein, a molecular beacon, a luminescent compound or particle and a combination of two or more thereof. In addition, for various embodiments of the invention, the reporter tags are chemically or physically interconnected to a particle of suitable size and the reactive part of the reporter tag is capable of binding soluble factors contained in the sample.

In accordance with at least one embodiment of the invention, the excitation laser or source comprises a helium-neon gas laser having a wavelength of about 632.8 nm, the means for detecting is optimal for a wavelength range of between about 620 nm and 850 nm, and the sample comprises whole blood.

In accordance with various embodiments of the present invention, the sample comprises at least one SERS-particle.

In accordance with various embodiments of the present invention, the means for detecting comprises on-chip 2-D binning.

In accordance with another embodiment of the present invention, an apparatus for performing laser scanning on a sample having particles in a suspension is provided, the apparatus comprising one or more sources of excitation source, a scanner to direct the excitation source through the sample, an objective to collect light emitted by the sample in response to the excitation source, a spectrograph to disperse the emitted light over a plurality of wavelengths as a spectrum, and a charge coupled device for detecting the spectrum. In addition, in accordance with various embodiments of the present invention, the charge coupled device produces a readout pattern that can be changed in real-time by reformatting (a) a number of simultaneous detection channels, and (b) a spectral bandpass of at least one of the one or more detection channels.

In accordance with various embodiments of the present invention, the objective comprises an F-Theta scan lens to focus the excitation source into the sample and confocally collect the light emitted in response to the delivered excitation source. In addition, in accordance with at least one embodiment, the F-Theta scan lens comprises a focal length of about 6.8 mm, a numerical aperture of about 0.55, and a magnification of about 20.

In accordance with various embodiments of the present invention, the objective, at least one afocal lens pair, and the spectrograph provide a magnification appropriate to image the scanned particles onto a two-dimensional surface of the charge coupled device.

In accordance with various embodiments of the present invention, the spectrograph comprises a concave holographic grating.

In accordance with another embodiment of the present invention, a method for performing scanning of a sample is provided, the method comprising applying an excitation source to the sample, collecting light emitted by the sample in response to the excitation source, dispersing the emitted light over a plurality of wavelengths as a spectrum, and detecting the spectrum using a charge-coupled device. In addition, the method may further comprise tagging the sample with at least one tag selected from the group consisting of a surface enhanced Raman scattering tag, a fluorescent organic tag, a fluorescent protein tag, and a quantum dot tag.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

DETAILED DESCRIPTION OF THE INVENTION

The present invention comprises a CCD-based laser scanner that provides spectral flexibility needed for the spectrocopic monitoring of highly multiplexed cellular and particle assays in whole blood or other suspensions. In one embodiment, the present invention comprises a CCD-based microvolume laser scanning cytometer (MLSC) for monitoring cells in whole blood and other suspensions. However, it is to be understood that the present invention has application to monitoring objects or particles other than cells in blood. By way of example and not limitation, the CCD-based laser scanner may be used to monitor non-cell particles in a liquid, such as beads or other man-made particles in a liquid suspension. As further examples, the CCD-based laser scanner may be used to interrogate immunoassays in a buffer, or particles and reporter tags attached to a flat surface, such as microscope slides.

The present invention allows for the real-time reconfiguration of the number of detection channels and the spectral band pass of each of the detection channels. This makes the present invention suitable for use with a wide variety of fluorescence tags, including traditional fluorophores and Qdots. The unique properties of the detector configuration of the present invention allows, for the first time, to specifically take advantage of the fine spectral features and multiplexing capabilities of SERS tags.

For puproses of providing an illustrative example of a preferred embodiment, a CCD-based MLSC system is described herein. However, it is to be understood that CCD-based non-MLSC systems are within the scope of the current invention and form part of the claims herein.

The CCD-based MLSC system embodiment of the present invention shares elements of the MLSC system described in U.S. Pat. No. 6,687,395 including some hardware components, disposables and software. See Norton et al., 2000, "Cell Enumeration and Characterization in Microvolume Laser Scanning Cytometry: A Multicolor Image Processing Package," *IBOS Society of Photo-Optical Instrumentation Engineers*, p 20-30, incorporated herein by reference in its entirety. The optical and mechanical front-end of the MLSC system of U.S. Pat. No. 6,687,395, for example, may be substantially unchanged in the CCD-based MLSC system of the present invention. However, a number of changes and improvements are provided in the present invention, as described below.

Figure 1:
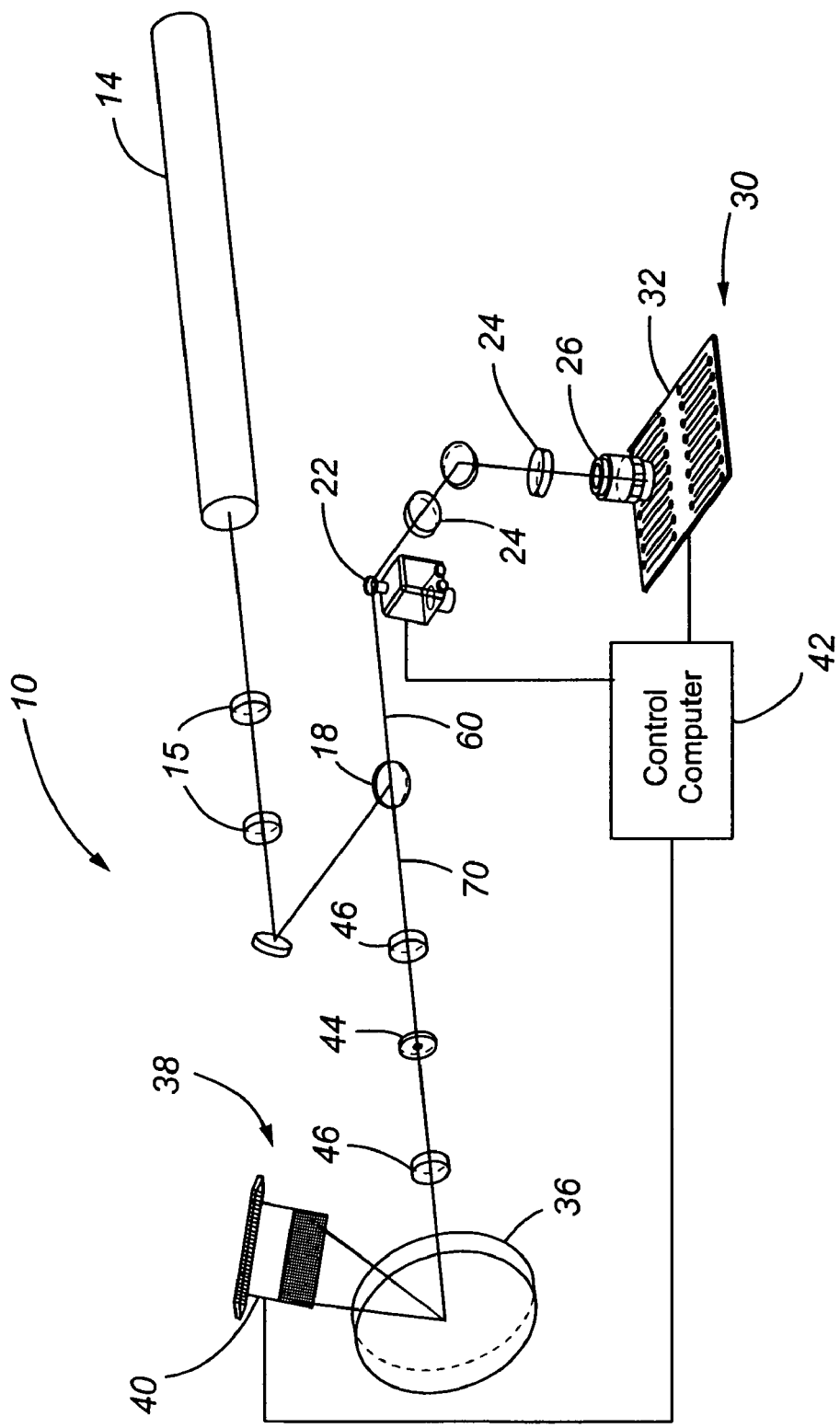
FIG. 1 depicts an optical layout of an embodiment of the present invention in partial block and diagrammatic form.

In accordance with embodiments of the present invention, FIG. 1 depicts an optical layout of a CCD-based MLSC system 10. The CCD-based MLSC system 10 comprises an excitation light source 14, an afocal lens pair 15, an excitation dichroic filter 18, a galvanometer-driven scan mirror 22, a second afocal lens pair 24, an objective 26, and a sample array 30. These components comprise the excitation path 60 of the present invention. In addition, embodiments of the present invention also comprise optical elements that, in their entirety, make up the detection path. Elements of the CCD-based MLSC system 10 belonging to the detection path 70 are the objective 26, the afocal lens pair 24, the excitation dichroic 18, a third afocal lens pair 46, a pinhole 44 positioned at the internal focus of the afocal lens pair 46 and an imaging spectrograph 36 comprising a dispersive element with a finite focal length, and a CCD detector 38. Excitation light traverses along the optical path of the system from the excitation source 14 towards the sample array 30. Emitted light traverses along the optical path of the present invention from the sample array 30 towards the CCD detector 38. While substantially all of the excitation light is reflected off the excitation dichroic 18, the majority of the emitted and collected light passes through said excitation dichroic 18. The CCD detector 38 detects the spectrally dispersed emission light simultaneously in one or more detection channels according to its wavelength.

In general, the excitation light source 14 is an excitation laser demonstrating good performance for the CCD-based MLSC system 10. In accordance with embodiments of the present invention, and by way of example and not limitation, the CCD-based MLSC system 10 uses a Helium-Neon gas laser (632.8 nm emission wavelength) as the excitation light source 14. Other laser options include solid-state diode lasers with emission wavelengths around 635 nm. Both types of laser sources are suitable for the present invention, if they deliver at least 5 mW to the sample.

The collimated laser light from the excitation light source 14 may be directed through an afocal lens pair 15 in order to achieve the beam diameter that is necessary for the afocal lens pair 24 and the objective 26 to focus the beam into a spot of appropriate size for imaging the particles of interest.

The excitation beam then is deflected by the excitation dichroic filter 18. Upon reflection, the light is incident on the galvanometer-driven scan mirror 22. The scan mirror can be rapidly oscillated over a fixed range of angles by the galvanometer. The scanning mirror reflects the incident light into two relay lenses 24 that image the excitation light or excitation laser beam onto the entrance pupil of the objective 26 that focuses the excitation light onto the sample.

The sample array 30 can comprise a variety of sample containment structures, such as microtiter plates, slides having a flat surface, and volumetric capillaries. A volumetric capillary enables the gathering of absolute cell counts, such as values in cells/µl. In accordance with one preferred embodiment, the present invention comprises a capillary array 32 that contains samples for analysis.

Figure 2A:
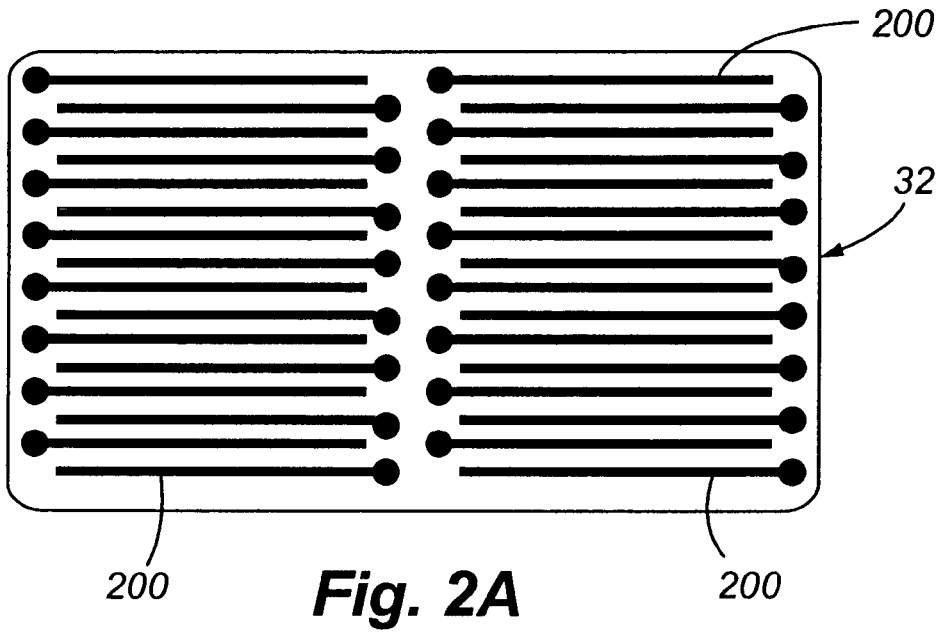
FIG. 2A is a plan view of a sample array in accordance with embodiments of the present invention.

Referring now to FIG. 2A, an example of a capillary array 32 is shown. Disposable capillary arrays may be used with the CCD-based MLSC system 10. Disposable capillary arrays are assembled from layers of low-fluorescent polycarbonate sheets and adhesive. The example capillary array 32 in FIG. 2A holds 32 assays and has 9 mm fill hole spacing for compatibility with multi-channel pipettes. Each capillary 200 is about 53 mm in length, 1.8 mm in width and 135 µm in depth.

Figure 2B:
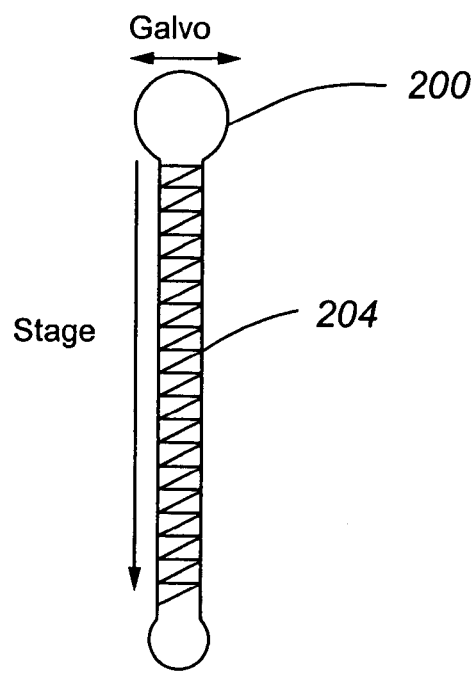
FIG. 2B is a plan view of a capillary and a scanning pattern in accordance with embodiments of the present invention.

Referring now to FIG. 2B, a scan pattern 204 over a single capillary 200 is shown. In one preferred embodiment, the scan pattern 204 comprises raster scanning. In use, as for example, when scanning whole blood, the capillary 200 is filled with whole blood that has been stained or otherwise prepared with reporter tags. The scan area is about 1 mm wide and typically 40 mm long. In accordance with embodiments of the present invention, a galvanometer moves the laser beam across the short dimension of an individual capillary 200 while the stage or sample array 30 moves in the long dimension, thus providing a means for scanning the sample. Alternatively, a first galvanometer-mirror can implement one axis of the raster-scan across a surface of the capillary 200, and a second galvanometer-mirror can implement a second axis of the raster scan. In use, successive capillaries are typically scanned in order.

Referring again to FIG. 1, in accordance with embodiments of the invention, and by way of example and not limitation, the CCD-based MLSC system 10 utilizes an F-Theta scan lens. Although the objective does not necessarily have to be a F-Theta lens, this type of lens has been found to be advantageous for light collection. The F-theta scan lens, may, for example, comprise a numerical aperture of 0.1 to 1.5, with a magnification of 5 to 100, or up to 400. In addition, the lens may have a working range between about 1 to 10 mm. These ranges provide appropriate imaging characteristics depending upon the particle size being scanned. For example, an F-Theta lens used with a CCD-based system may comprises a working length of about 6.8 mm, a numerical aperture of about 0.55, and a magnification of about 20. However, as will be appreciated by those skilled in the art, it is to be understood that this is only an example, and different lens types with different optical characteristics may be used with the current invention if appropriately chosen.

In general, the F-Theta scan lens should be selected for providing the optimal combination of numerical aperture, working distance, magnification, optical distortion and aberrations. Together with all other beam shaping elements—such as the afocal lens pairs 15 and 24, that may or may not be part of the embodiment of the invention—the objective focuses the excitation beam into a focal spot with a diameter appropriate for the imaging the objects, cells or particles in the sample. Since the objective 26 also collects the light emitted in response to the delivered excitation light, the present invention works in confocal mode. It is to be understood that embodiments of the present invention may be configured so that the objective does not operate in a confocal mode, such as where a first objective is used for focusing the excitation light though the sample, and a second properly positioned objective is used to collect the emitted light.

For an objective 26 operating in confocal mode, keeping the numerical aperture as high as possible increases the light collection efficiency, which helps achieving high instrument sensitivity. The high collection efficiency also provides a means for keeping the laser power at a minimum, advantageously avoiding accelerated photo bleaching of the sample. A high numerical aperture also decreases the depth of field, and thus reduces the fraction of out-of-focus light that enters the system. Choosing an F-Theta lens over a conventional microscope objective maintains a high imaging quality across the full field of view. The characteristics of this type of lens keeps the exiting beam substantially parallel to the optical axis across all scan angles. As a result, the focus spot-size remains substantially constant and circular, even when the beam scans a capillary near the edge of the field of view. This is not the case for conventional microscope objectives, for which optical aberrations may cause the focus spot-size to increase and take an elliptical shape near the outer edges of the field of view. An increase in spot-size during the scan potentially lowers the photon flux [photons $m^{-2}sec^{-1}$] delivered to the tag, and thus, will result in a decrease of the emitted fluorescence signal. Accordingly, the objective 26 of the current invention overcomes these difficulties.

The optical elements leading to the sample, including the objective 26, influence the spot-size at the sample. In general, the diameter of the focused laser beam must be less than or equal to the mean radius of the cells or particles being scanned. A larger spot-size will not enable the cells or particles to be imaged. However, although smaller spot-sizes could increase the image quality, if the spot-sizes are substantially smaller than the mean radius of the cells or particles being scanned, then the scan speed is decreased, providing lower throughput, which is not desirable.

Referring to FIG. 1, an additional afocal lens pair is inserted in the optical path after of the excitation dichroic 18 and before the imaging spectrograph 36. A pinhole 44 is positioned at the internal focal point between the two lenses comprising the afocal lens pair 46. The pinhole 44 controls the depth-of-field and its diameter is chosen to prevent a substantial portion of the out-of-focus light from reaching the CCD detector 38 while increasing the signal-to-noise ratio. The second function of this afocal lens pair 46 is the adjustment of the diameter of the collimated beam such that it is optimal for the numerical aperture of the dispersion grating of the spectrograph 36 and helps achieving the targeted system magnification.

As described above, the detection path of the CCD-based MLSC system 10 also comprises an imaging spectrograph 36 and a CCD detector 38. In accordance with embodiments of the present invention, the imaging spectrograph 36 serves as a means for spectrally dispersing the collected emission light and the means for imaging the spectrum. In combination, the objective 26, the afocal lens-pairs 24 and 46, and the spectrograph 36 provide an appropriate magnification to image the scanned objects, cells or particles onto the two-dimensional surface of the CCD detector 38.

In general, the spectrograph 36 is adapted for effectively dispersing the collected light over a spectral range of 200 nm or more, beginning from the wavelength of the excitation laser and continuing to longer wavelengths. However, it is to be understood that spectrographs of different design may be used, and such devices are within the scope of the present invention.

In accordance with embodiments of the present invention, and by way of example and not limitation, the spectrograph 36 may comprise a flat-field holographic concave grating with 230 lines/mm, a blaze wavelength of 875 nm, and a radius of curvature of 139.19 mm. The concave grating does not just simply disperse the light, but it focuses the spectrum at the same time. In contrast, a prism expands the spectrum infinitely without ever going through a focal plane. Thus, the preferred structure of a concave grating makes an imaging spectrograph. Alternatively, the means for spectrally dispersing and the means for imaging may be a modified Czerny-Turner spectrograph, comprising two toroidal mirrors and a planar diffraction grating.

The CCD detector 38 is located at the focal plane of the imaging spectrograph 36 and provides a means for detecting the spectrally dispersed emission light. Accordingly, the CCD detector 38 receives the spectrum of light generated by the imaging spectrograph 36. In accordance with embodiments of the present invention, and by way of example and not limitation, the detector may be a CMOS sensor, or an off-the-shelf scientific CCD-camera (SciMeasure Analytical Systems, Decatur, Ga.) may be used as the CCD detector 38. It consists of the detector head 40, which includes a CCD-67 dual stage Peltier-cooled CCD (e2v Technologies, Chelmsford, England) and the electronics module, which controls the CCD-readout process and interfaces with the control computer 42. As placed in the focal plane of the present invention, and as a result of the combination of system magnification, optical filters 18, size of the pinhole 44, dispersive power of the spectrograph 36 and its own pixel size, the CCD detector 38 receives an image of the spectrum of the emitted light, as for example, in the wavelength range between 635 nm and 850 nm. The detected spectrum extends over approximately 130 CCD-pixels in the direction of the spectral dispersion and about 10 pixels in the direction orthogonal to the spectral axis.

Figure 3:
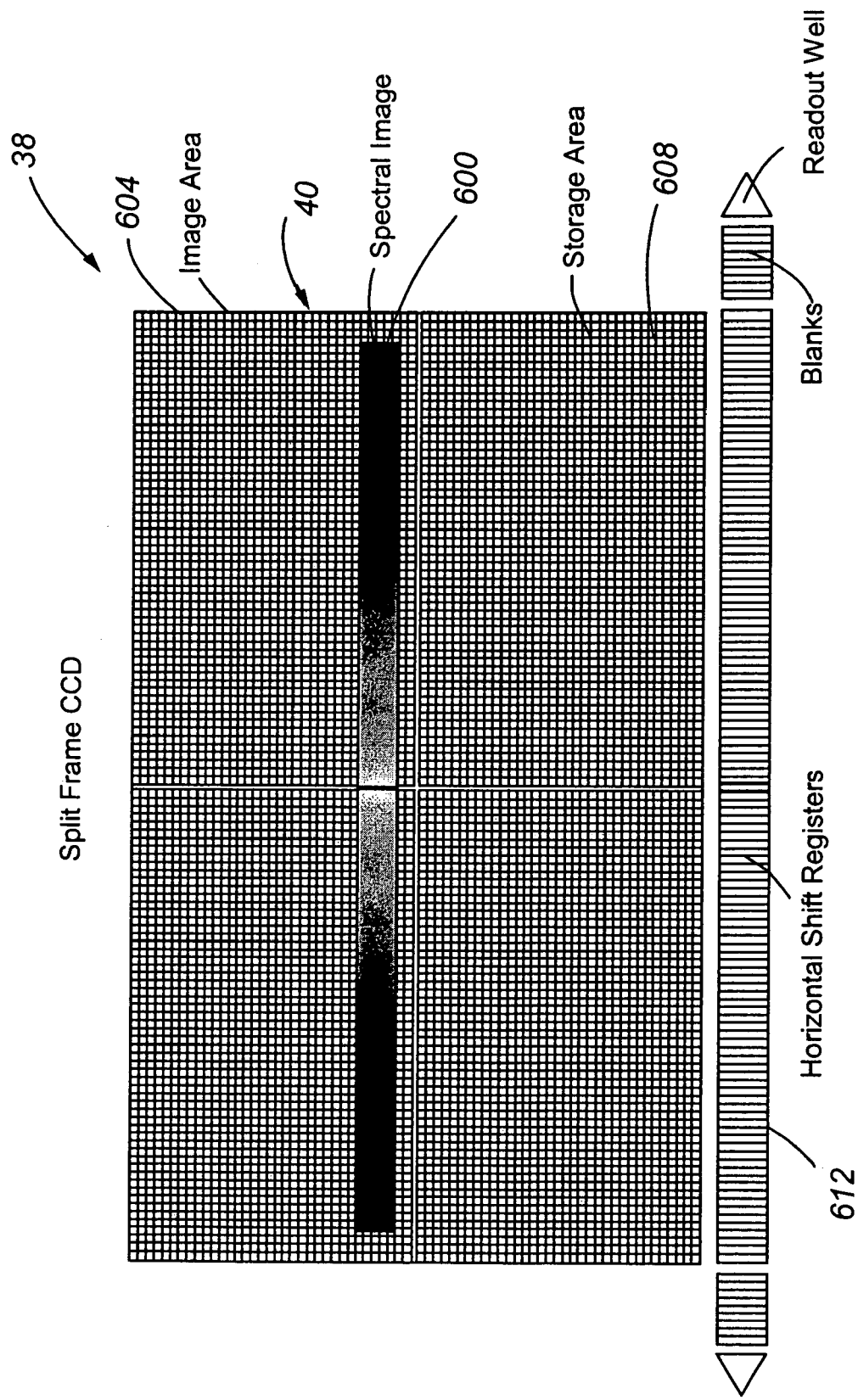
FIG. 3 is plan view of a CCD detector in accordance with embodiments of the present invention.

Referring now to FIG. 3, an example of a CCD detector 38 is shown with a spectral image 600 superimposed on the CCD detector 38. The CCD detector 38 has an image area 604 comprising a two-dimensional surface. The image area 604 is shielded from substantially all light but the spectrum, including stray light, scattered light and ambient light. The pixels of the image area 604 capture the image of the spectrum. During the readout process, the pixel content is shifted vertically across the shielded storage area 608 into the horizontal shift register 612 for final readout. Certain CCD-architectures implement a split-frame design with two or more readout amplifiers. The two simultaneous readout nodes double the effective data rate.

It is to be understood that other components may be used to maximize the collection efficiency, and such devices are within the scope of the current invention. This includes using steep edge filters for the excitation dichroic 18.

In accordance with embodiments of the present invention, all aspects of the CCD-based MLSC system 10 may be controlled through a desktop PC based application or control computer 42 using the MICROSOFT WINDOWS® operating system or a Linux operating system. A motion-control PC-expansion board is preferably used to control the stage movements. A multi-function IO-board is preferably used to control the scanning motion of the galvo-mirror 22, synchronize the CCD dectector 38 with the galvo scan and control additional camera functions. A digital frame grabber board is preferably used to receive the data values from the main camera driver board. In addition, the CCD-based MLSC system 10 preferably uses a single software application to control all aspects of the instrument data acquisition process. In particular, the software implements control over the CCD-binning and color channel definition in real time. In this way, fluorescence tags can be changed as needed for optimal assay performance. Software changes related to instrument control can be performed as part of a graphical user interface.

Figure 4A:
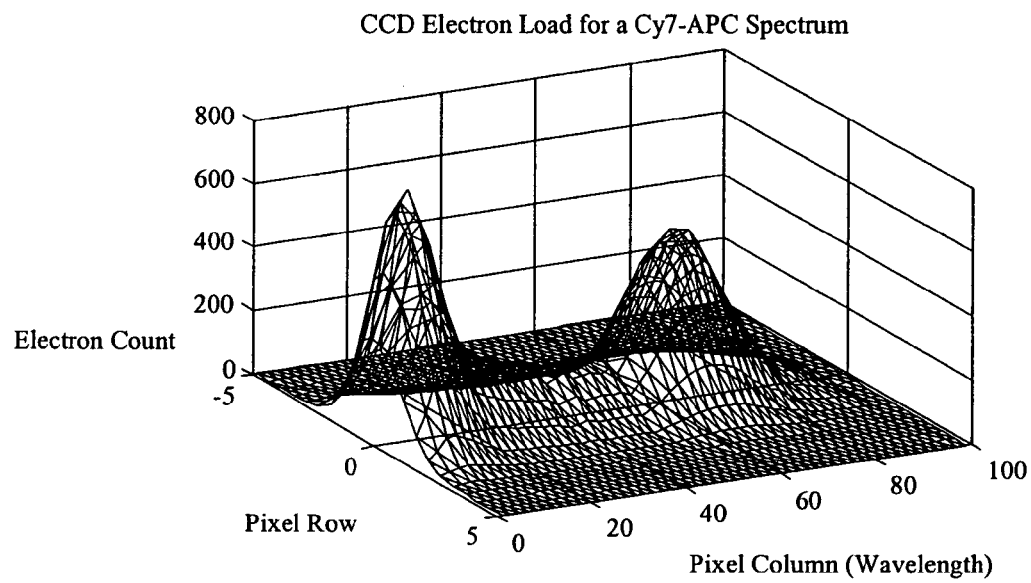
FIG. 4A illustrates an example of imaging a fluorescent dye spectrum onto a CCD.
Figure 4B:
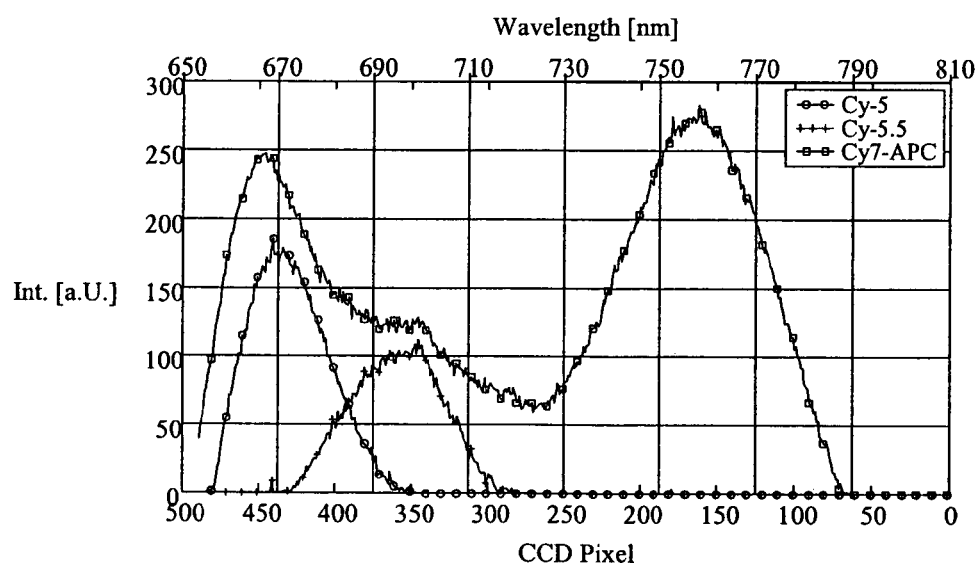
FIG. 4B illustrates 1D-binning (i.e., summing all pixel rows in the horizontal shift register before reading out the charge) of the imaged fluorescent dye spectrum in FIG. 4A.

Referring again to FIGS. 3, 4A and 4B, performance constraints inherent to the basic CCD-design, such as a relatively limited dynamic range and a comparably low readout speed have been overcome by the appropriate layout of the detection structures and operation of the CCD detector 38. As noted above, the CCD detector geometry for one embodiment is shown in FIG. 3. The CCD is positioned in the focal plane of a flat field imaging spectrograph 36 such that the spectrum is projected across the image area of the CCD, with the dispersion (spectral) axis of the spectrum extending across the CCD. More preferably, the CCD-based MLSC system 10 is configured such that the spectrograph 36 is positioned to focus the spectrum of the collected emission light onto the CCD detector 38 with the dispersion direction oriented substantially parallel to the shift register of the CCD detector. In one embodiment of the invention, the optical system preceding the detector ensures a cross-sectional width of the spectrum of about 0.26 mm, or as shown in FIG. 4A, the spectrum covers 10 pixel rows of the CCD detector. More particularly, FIG. 4A illustrates an example of imaging a fluorescent dye spectrum onto a CCD. The spectrum creates a Gaussian intensity cross-sectional profile (pixel rows) with the spectral wavelength in the other direction (columns). As the CCD is read out, the pixel rows are transported from the top of the CCD down through the shielded storage area into the horizontal shift register. There, the charge of ten rows is accumulated before the shift register pixels are horizontally shifted towards the readout wells of the CCD. This process of charge accumulation in the shift register is called 1D-binning, and is shown in FIG. 4B. 1D-binning (i.e., summing all pixel rows in the horizontal shift register before reading out the charge) creates spectra comparable to traditional linear-array photo-diode spectrometers. For the example shown, 500 pixels (lower axis) cover a wavelength range of approximately 160 nm (upper axis). Depending on the speed requirements, an additional 2D-binning step can be implemented by accumulating the charge of several shift register pixels in the summing well before reading out the summing well. Implementing on-chip 2D-binning decreases the resolution of the acquired spectra while still preserving the spectral shape of the dye spectra. 2D-binning can increase CCD-data rates to levels comparable to traditional PMT-detectors. For the information shown in FIGS. 4A and 4B, measurements were made with a custom designed Czerny-Turner spectrograph.

A parameter for characterizing the readout speed of the CCD detector 38 is the effective data rate. The effective data rate is the time it takes to read out one data point for each color channel and depends on the size of the spectral image, the number of color channels and the pixel clock rates. For a 5-channel setup and using typical operational parameters for a CCD-67 (E2V, Inc.), effective data rates of up to 100 kHz can be achieved depending on the type of implemented on-chip binning. In comparison, a PMT-based MLSC instrument typically operates at 64 kHz and can achieve up to 256 kHz for a few select assays. In accordance with embodiments of the present invention, the readout pattern of the CCD detector 38 can be changed in real-time by reprogramming the clock-drivers of the CCD detector.

In use, samples are prepared with the various desired tags and then loaded into the structure holding the sample 30, such as a capillary array 32. The excitation light source 14 is then activated by the control computer 42, and the excitation light is transmitted along the excitation path 60 to the sample or sample array 30. The objective 26 is used to scan the excitation light to the sample array 30, and also to confocally collect the light emitted from the sample. The control computer 42 operates the galvanometer-driven scan mirror 22 and the sample array to provide a scan pattern, such as raster scanning of the sample. The emitted fluorescence or scatter light from the sample travels along the detection path 70, which is divided from the excitation path 60 by the excitation dichroic filter 18. The emitted light impinges on spectrograph 36, which disperses the emitted light over a plurality of wavelengths as a spectrum. The image of the spectrum is then detected on the CCD detector 38.

Implementation of a CCD-based (all solid-state, low voltage) detection system significantly simplifies the hardware components of the CCD-based system over that of the previously available MLSC systems. The four-times higher quantum efficiency of the CCD over the PMT allows a significant decrease in the excitation laser power, thus decreasing photo-bleaching and non-linear triplet-state effects. Speed limitations inherent to the CCD-design are overcome by the optical configuration of the present invention. In addition, a 2D-binning mode can be utilized to improve speed. Projecting the spectral image across a long, but narrow, section of the CCD-detector, creating a high aspect-ratio image/spectrum, helps offset the dynamic range limitations of the CCD-detector. While the detection channels for a PMT based instrument are difficult to change, the CCD-based setup enables the operator to change the number of detection channels, its location and spectral width in real-time, simply by re-programming the camera electronics. This represents a significant advantage for instruments with highly multiplexed assays and mixed fluorescence sources (organic dyes, Qdots, SERS-tags). Moreover, the instrument is especially well suited to evaluate new tags.

The CCD-based laser scanning system of the present invention is able to evaluate a number of types of tags, including SERS, fluorescent organic and protein tags and Qdot tags, and can be used to identify and rank appropriate individual and sets of tags for a variety of assays. This may be performed, for example, by preparing streptavidin and antibody reagents with tags from each class and evaluating them on beads and cells. Reagents can be compared based on signal-to-noise, non-specific binding and compatibility with the instrument and each other. Table 1 provides a (non-exhaustive) list of small molecule, protein, quantum dot and SERS tags that are available for such assays, and their excitation and emission properties.

TABLE 1

Organic, Qdot and SERS tags

| DYES | EX (nm) | EM (nm*) |
|---|---|---|
| Small molecule TAGS | | |
| Cy5 | 649 | 670 |
| Cy5.5 | 675 | 694 |
| Alexa-633 | 632 | 647 |
| Alexa-647 | 647 | 665 |
| Alexa-660 | 663 | 690 |
| Alexa-680 | 679 | 702 |
| Alexa-700 | 702 | 723 |
| Alexa-750 | 749 | 775 |

TABLE 1-continued

Organic, Qdot and SERS tags

| DYES | EX (nm) | EM (nm*) |
|---|---|---|
| Small molecule TAGS SERS TAGS | | |
| BPE | 633 | 705 |
| MGITC | 633 | 650 |
| Other SERS | 633 | Vary |
| Protein and Tandem Tags | | |
| APC | 650 | 660 |
| Alexa-680-APC | 760 | 702 |
| Alexa-700-APC | 650 | 723 |
| Alexa-750-APC | 650 | 775 |
| Cy7-APC | 650 | 767 |
| Quantum Dots | | |
| Qdot-655 | Many | 655 |
| Qdot-705 | Many | 705 |
| Other Qdot | Many | vary |

*Peak light wavelength in units of nanometers.

Traditional small molecule fluorophores may be used with the CCD-based system of the present invention. Traditional small molecule fluorophores include the red emitting Cy (Amersham) and Alexa (Molecule Probes) dyes. All are readily conjugated to antibodies via NHS chemistry and have been used in the laboratory. Proteins (e.g., APC) and tandem dyes (protein-small molecule conjugates like Cy7-APC) are also in routine use in the lab and can be coupled to antibodies via the hinge region sulfhydryl groups. It is believed that four to six traditional dyes (small molecules, protein, tandem) can be used on the CCD-based MLSC 10 embodiment of the invention at once.

Quantum dots (or "Qdots") are also appropriate for use with the CCD-based system of the present invention. Currently there two types of Qdot tags in this region of the spectrum: Qdot-655 with a CdSe core and Qdot-705 (Quantum Dot Corp., Hayward, Calif.) that contains a CdTe component and has a rather broad spectrum. Given a relatively modest bandwidth of 30 nm, it is believed that up to six red-emitting Qdots can be used on the CCD-based MLSC of the invention, if they are prepared at the appropriate wavelengths and band pass.

Figure 5:
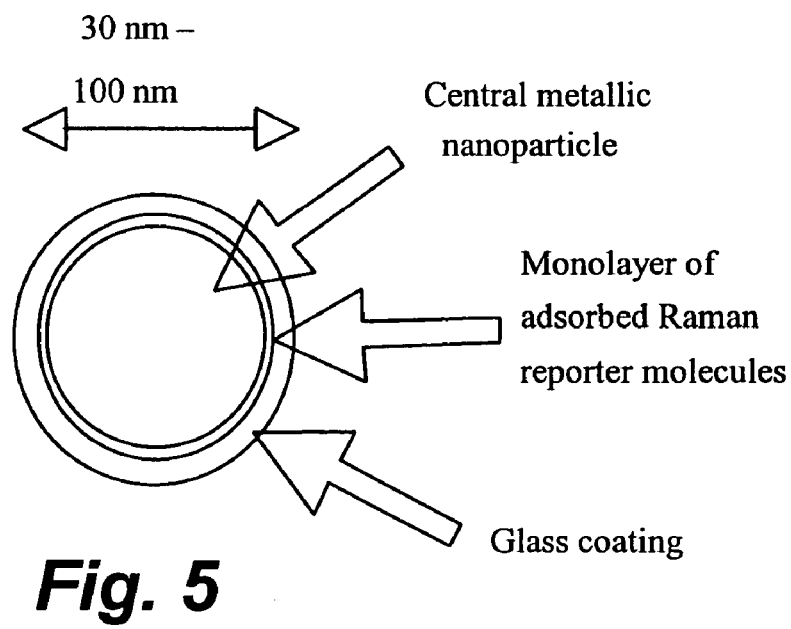
FIG. 5 depicts SERS nanotag structure.

SERS tags may be prepared and used for cellular assays with the CCD-based system of the present invention. FIG. 5 depicts SERS nanotag structure. The basic structure is shown for a composite SERS nanotag, comprising a metallic nano-particle, a layer of Raman reporter molecules and a glass coating. Reactive groups on the glass coating enable conjugation to antibodies, and so on. The composite SERS tags used with the CCD-based scanner of the present invention can use labeling of metal nanoparticles with Raman reporter molecules. To make the labeled particles robust, the surface is preferably coated with glass (or other appropriate encapsulants). The glass serves to both protect the Raman label from the environment and to provide an anchor for particle functionalization. Glass encapsulated SERS nanotags can be functionalized in many ways. For example, the SERS nanotags may be modified by reaction with aminopropyltrimethoxysilane to present amines. Heterobifunctional crosslinking reagents may then be used to couple antibodies to the tags via the hinge region sulfhydryl groups. The glass can also be made biocompatible, e.g., with a hydrophilic coat, to minimize non-specific binding in cellular assays. Currently there are two types of SERS tags (BPE and MGITC) that are ready for conjugation to streptavidin and antibodies. It is expected that a large number of tags (e.g., 30) may be used on the CCD-based system of the present invention.

Figure 6:
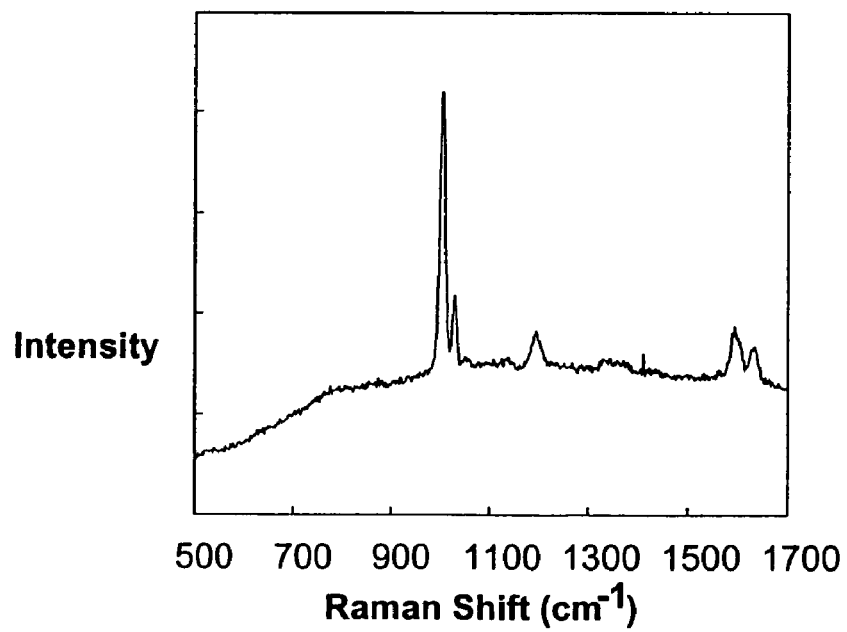
FIG. 6 illustrates surface-enhanced Raman scattering (SERS) spectrum of pyridine.

FIG. 6 illustrates surface-enhanced Raman scattering (SERS) spectrum of pyridine. Raman spectra are reported as the shift from the excitation wavelength in units of wavenumber (cm-1) rather than absolute nm, as is common for fluorescence spectroscopy. Given an excitation wavelength of 633 nm, the spectral shift range shown on the x-axis corresponds to 653 to 709 nm.

Conjugates are also appropriate for use with the CCD-based system of the present invention. Antibodies available from commercial vendors (e.g., BD Pharmingen, Beckman Coulter, Serotec), as well as streptavidin, are presented in Table 2. Conjugated reagents can be titrated on whole blood and erytrhocyte-lysed blood in both homogeneous (no wash) and washed modes. Cy5, Cy5.5, Cy7APC and some of the Alexa dyes have been conjugated to these antibodies.

TABLE 2

Example Antibody Test Set

| Target Antigen | Cell Type | Comment |
|---|---|---|
| Streptavidin | Biotin beads, secondary cell staining | Standard beads enables evaluation independent of biology |
| CD3, CD4, CD8 | T cells | CD4 is present at lower levels on monocytes than T cells and is good for comparison |
| CD20 | B Cells | Bright staining |
| CD14 | Monocytes | Compare with CD4 on monocytes |
| CD16 | Granulocytes | Bright staining |
| CD45 | All leukocytes | Bright staining |

Combinations of tags are also appropriate for use with the CCD-based system of the present invention. It is possible to mix-and-match the different classes of tags: organic, Qdot and SERS. The large number of effective detection channels, together with ability to change both the number and spectral definition of the detection channels in real-time enables advanced approaches to compensation for spectral overlap. This is particularly useful for SERS tags that have nonadjacent spectral features. Since Raman tags tend to have discontinuous spectral features, the CCD-based system, with pixels that can be grouped into discontinuous channels, is ideally suited for detection of these tags. The many effective channels are available by dividing the spectra into more units than is conducted in current practice (3-5), which enables advanced approaches to compensation for spectral overlap.

The present invention also provides a method for evaluating the use of multiple tags in cellular bioassays, including cell surface staining and intracellular for both cytokines and phosphorylated proteins. In this way, a range of multi-color assays on whole blood and PBMCs may be performed.

A range of cellular assays are available using the CCD-based MLSC system of the present invention. The assays may use sets of tags that are relevant to analysis of the immune system, for example. Cytometry assays and reagents have been developed for both flow and laser scanning systems. See Kantor et al., 1996, "FACS Analysis of Leukocytes," In: Herzenberg L A, Weir D M, Herzenberg L A, Blackwell C, editors, *Weir's Handbook of Experimental Immunology*, 5th ed. Volume 2. Cambridge, Mass.: *Blackwell Science*; p 49.1-49.13, the contents of which are incorporated by reference in its entirety. Clinical studies with MLSC systems have used panels of 64 three-color cellular assays, arranged in two disposable capillary arrays, that allow the identification and enumeration of hundreds of different cell types and cell-associated molecules that are relevant to immune, inflammatory and metabolic processes. Each reagent cocktail typically contains one or two antibodies to the major cell populations—neutrophils, eosinophils, monocytes T cells, B cells, NK cells, and platelets—and one or two antibodies to subsetting antigens which may indicate the functional state, activation state or adhesion characteristics of the population. About 100 cell surface and intracellular 3-color assays are available for the CCD-based system. Most of these assays use Cy5, Cy5.5 and Cy7APC and to a lesser extent the Alexa dyes. A (nonexhaustive) list of available target antigens are provided in Table 3.

TABLE 3

Example Set of Target Antigens

| Major Cell Population | Major Marker | Subsetting Antigen |
| --- | --- | --- |
| T Cells | CD3 CD4 CD8 | CD2, CD5, CD6, CD7, CD25, CD26, CD27, CD28, CD38, CD44, CD45RA, CD45RB, CD57, CD60, CD62L, CD69, CD71, CD86, CD89, CD95, CD127, CD161, TCR αβ, γδ, CCR5 |
| B Cells | CD19, CD20 | CD5, CD38, CD40, CD62L, CD69, CD71, CD72, CD80, CD86, CD95, HLA-DP, DQ, DR, PAN |
| NK Cells | CD56, NKB1 | CD2, CD7, CD8, CD57, CD161 |
| Granulocytes, Eosinophils | CD15, CD16 | CD18, CD32, CD44, CD64, CD52 CD66b, CD89, CD119, CD123 |
| Monocytes | CD14 | CD4, CD11b, CD33, CD38, CD44, CD54, CD86 CD95, HLA-DP, DQ, DR, PAN, TLR2, TLR4 |
| Platelet, other | CD41a, CD45 | CD61, CD53 CD62P; HLA-ABC, MOPC |
| Intracellular | Various above | Cytokines: IL-2, IL-4, IL-10, TNF-alpha, interferon beta Phosphoproteome ERK1/2, p38 MAPK, PLCγ1, Stat1, Stat3, Stat 5, Stat6, Zap70 Control: CD3 zeta |

Assays are built in layers, and individual regents can be titrated first, in homogenous (no wash) or washed assay modes as appropriate. In addition, combinations can be built sequentially from the titrated reagents: 2-color, 3-color . . . n-color.

Several articles have been published showing the cell surface staining for whole blood and other cell suspensions using the existing MLSC systems based on PMTs. See Kantor et al., 2004, "Immune Systems Biology: Immunoprofiling of Cells and Molecules," *BioTechniques*, 36:520-524; Kantor, 2002, "Comprehensive Phenotyping and Biological Marker Discovery," *Dis Markers*, 18(2):91-97; and Wyant et al., 2001, "Whole Blood Microvolume Laser Scanning Cytometry for Monitoring Resting and Activated Platelets," 12(5):309-318, the contents all of which are incorporated herein by reference in their entirety. A few additional applications relevant to the present invention are described below. These includes the use of both Qdots and SERS tags on the instrument.

Intracellular staining is desirable for monitoring cytokines or phosphor-specific proteins in the presence or absence of stimuli. Addition of fixation, permeabilization and washing steps enable the monitoring of both. Intracellular analysis can enable assessment of signaling pathways and correlation with biological and clinical parameters.

Indirect Qdot reagents are now commercially available from Quantum Dot Corp. As described herein, Qdot reagents are suitable tags for MLSC.

Figure 7A:
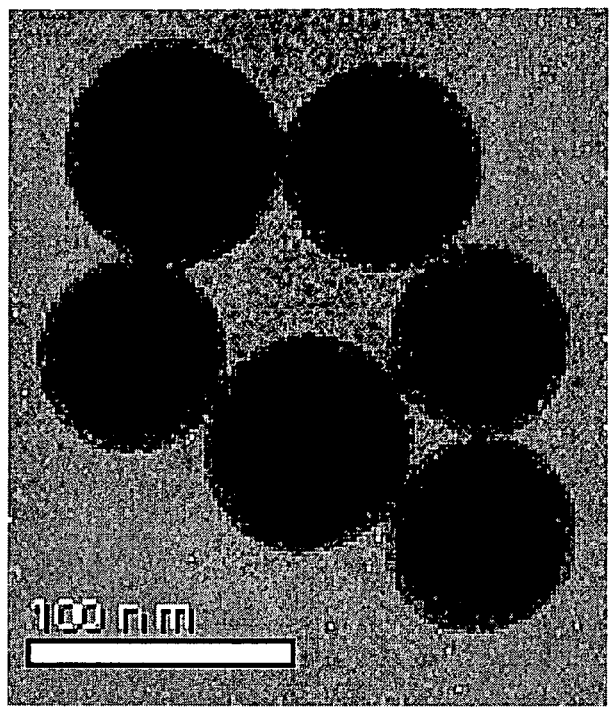
FIG. 7A illustrates a TEM image of silica-coated Ag nanoparticles.
Figure 7B:
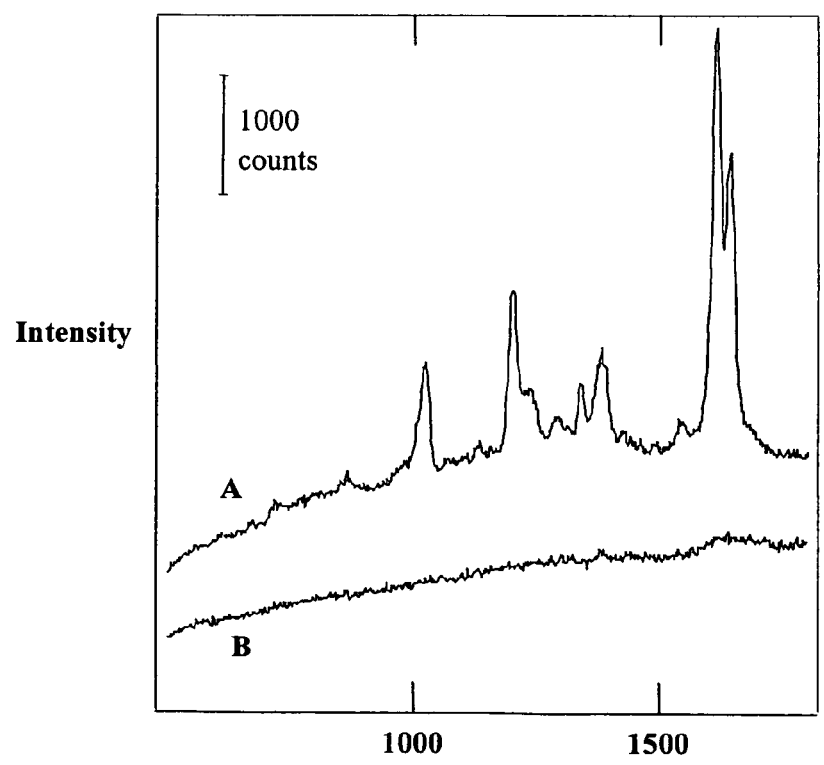
FIG. 7B illustrates the SERS spectra of a BPE labeled particle (A) and unlabeled control (B).

Referring now to FIG. 7A, the transmission electron microscopy (TEM) image of silica-coated Ag nanoparticles is shown. In FIG. 7B, the SERS spectra of a BPE labeled particle (A) and unlabeled control (B). Addition of 3-aminopropyltrimethoxysilane (APTMS) to a solution containing the desired Au or Ag nanoparticles made the particles vitreophilic. At this stage the Raman label was added (mercaptopyridine, or trans-1,2-bis(4-pyridyl)ethylene (BPE)) followed by the addition of sodium silicate to form the glass shell. The Raman spectra in FIG. 7B illustrate the signal generated by a BPE labeled particle (A), relative to the background seen with an unlabeled particle (B). In addition, the relative impermeability of the glass shell was illustrated by mixing BPE with 40 nm diameter Au colloid that had been coated with 11 nm of glass. In this case, where no SERS molecule had been specifically incorporated inside the glass shell, no SERS signal was seen.

Figure 8:
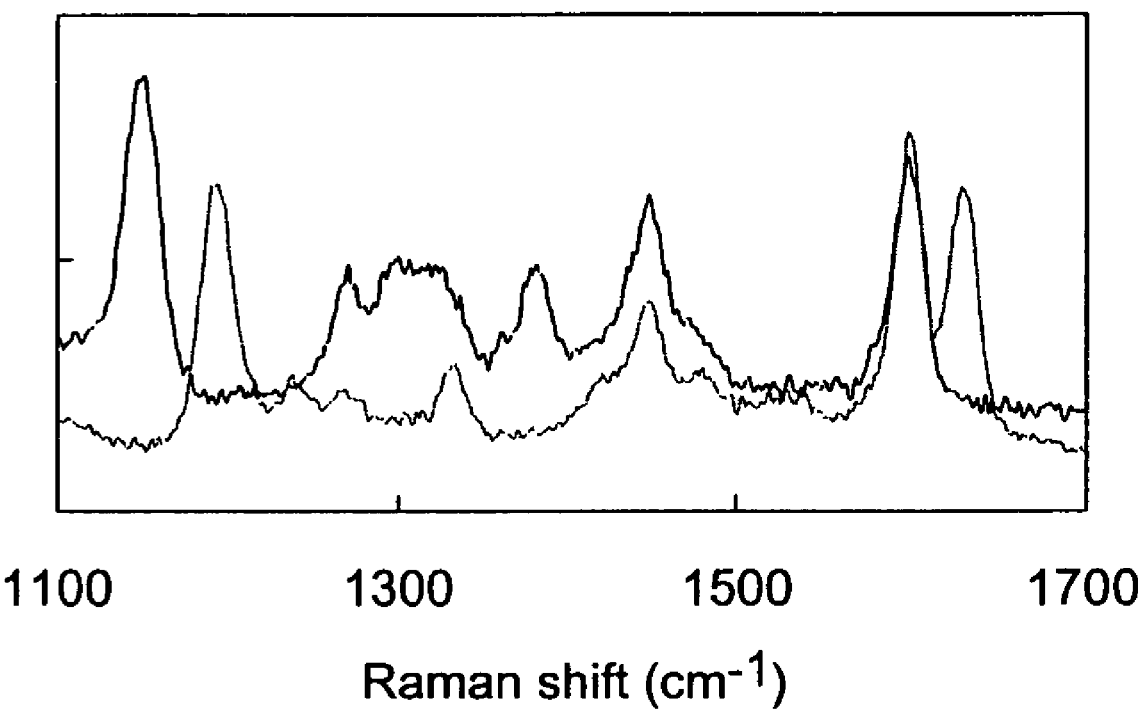
FIG. 8 illustrates Raman tag spectra for BPE on Au particle (gray line) and para-nitrosodimethylaniline on Au particle (black line).

The SERS spectra from closely related molecules can be clearly separated when those molecules are used as SERS tags. A small part of the spectra of BPE and para-nitrosodimethylaniline, both nitrogen-substituted aromatic rings, is shown in FIG. 8 which illustrates Raman tag spectra for two species: (i) BPE on Au particle (gray line) and (ii) PNDMA on Au particle (Black line). The spectra were obtained by depositing the tag molecule along with APTMS, on a gold colloid. After centrifuging the mixture and resuspending the particles, the spectra were obtained. Several features could be used to distinguish between the two molecules in this region of the spectra alone.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for performing laser scanning of a liquid sample containing particles, the system comprising:
   (a) means for scanning an excitation laser beam from an excitation laser across the sample;
   (b) means for focusing the excitation laser beam into the sample;
   (c) means for collecting a light emitted from the sample and its constituents in response to the excitation laser beam;
   (d) means for de-scanning the collected emission light;
   (e) means for spectrally dispersing the collected emission light;
   (f) means for imaging the spectrally dispersed emission light as a spectrum;
   (g) means for detecting the spectrum in one or more detection channels simultaneously according to its wavelength using a two-dimensional detector surface; and
   (h) at least one afocal lens pair in a beam path of the collected emission light between a dichroic mirror and the means for spectrally dispersing.

2. The system as claimed in claim 1, wherein the two-dimensional detector surface comprises a charge coupled device.

3. The system as claimed in claim 1, further comprising means for changing a readout pattern of the two-dimensional detector surface in real-time, wherein the means for changing effectively reformats (a) a number of simultaneous detection channels, and (b) a spectral bandpass of at least one of the one or more detection channels.

4. The system as claimed in claim 1, wherein the means for scanning and the means for de-scanning comprise a single galvanometer-mirror.

5. The system as claimed in claim 1, wherein the sample comprises suspensions selected from the group consisting of cells, man-made particles, and mixtures thereof.

6. The system as claimed in claim 1, wherein a structure holding the sample is selected from the group consisting of one or more capillaries having a known volume, one or more non-capillary containers comprising well plates, and one or more slides comprising a flat surface.

7. The system as claimed in claim 1, wherein the means for collecting, the means for spectrally dispersing, and the means for imaging provide a magnification appropriate to image the scanned particles onto the two-dimensional detector surface.

8. The system as claimed in claim 1, further comprising a pinhole at an internal focal plane of the at least one afocal lens pair, wherein the pinhole prevents a substantial portion of light emitted from outside a focal plane of the excitation laser beam from reaching the means for spectrally dispersing.

9. The system as claimed in claim 1, wherein the means for spectrally dispersing and the means for imaging is selected from the group consisting of (a) a concave holographic grating, and (b) two toroidal mirrors and a planar diffraction grating.

10. The system as claimed in claim 1, wherein the means for spectrally dispersing is adapted for a spectral range of 200 nm or more beginning from a wavelength of the excitation laser beam and continuing to longer wavelengths.

11. The system as claimed in claim 1, wherein the two-dimensional detector surface comprises a CMOS sensor.

12. The system as claimed in claim 1, wherein, except for the spectrum of the collected emission light emitted by the sample in response to the excitation laser beam, the two-dimensional detector surface is shielded from substantially all light.

13. The system as claimed in claim 1, wherein the two-dimensional detector surface is positioned in a focal plane of the means for imaging such that a dispersion direction is oriented substantially parallel to readout registers and shift registers of the two-dimensional detector surface, wherein the two dimensional detector surface is selected from the group consisting of a charge coupled device and a CMOS sensor.

14. The system as claimed in claim 1, wherein the means for detecting comprises on-chip 2-D binning.

15. The system as claimed in claim 1, wherein a readout pattern of the two-dimensional detector surface can be changed in real-time by reprogramming one or more clock-drivers.

16. The system as claimed in claim 1, wherein the means for scanning comprises means for raster scanning.

17. The system as claimed in claim 16, wherein a galvanometer-mirror implements one axis of the raster-scan across a surface of the sample.

18. The system as claimed in claim 1, wherein the means for focusing and the means for collecting comprise a common objective, wherein the common objective focuses the excitation laser into the sample and confocally collects the light emitted in response to the delivered excitation laser beam.

19. The system as claimed in claim 18, wherein the common objective comprises an F-Theta scan lens.

20. The system as claimed in claim 19, wherein the F-Theta scan lens comprises a focal length of about 6.8 mm, a numerical aperture of about 0.55, and a magnification of about 20.

21. The system as claimed in claim 1, wherein the sample comprises one or more reporter tags, the one or more reporter tags comprising at least one reactive component associated with one or more functional groups of interest of at least one of the particles in the sample, and at least one optically active component for absorbing photons with a wavelength of the excitation laser and emitting photons at a different wavelength.

22. The system as claimed in claim 21, wherein the at least one reactive component of the reporter tag is selected from the group consisting of an antibody, antigen, receptor, hapten, and lectin, and the at least one optically active component of the report tag is selected from the group consisting of an organic dye, a surface enhanced Raman scattering particle, a quantum dot, an up-converting phosphor, a fluorescent protein, a molecular beacon, a luminescent compound or particle and a combination of two or more thereof.

23. The system as claimed in claim 22, wherein the reporter tags are chemically or physically interconnected to a particle of suitable size and the reactive part of the reporter tag is capable of binding soluble factors contained in the sample.

24. The system as claimed in claim 1, wherein the excitation laser comprises a helium-neon gas laser having a wavelength of about 632.8 nm, and wherein the means for detecting is optimal for a wavelength range of between about 620 nm and 850 nm, and wherein the sample comprises whole blood.

25. The system as claimed in claim 24, wherein the sample comprises at least one SERS-particle.

26. An apparatus for performing laser scanning on a sample having particles in a suspension, comprising:
   (a) one or more sources of excitation source;
   (b) a scanner to direct the excitation source through the sample;
   (c) an objective to collect light emitted by the sample in response to the excitation source;
   (d) a spectrograph to disperse the emitted light over a plurality of wavelengths as a spectrum;
   (e) at least one afocal lens pair between a dichroic beam splitter and the spectrograph, wherein the dichroic beam splitter at least partially divides an excitation path and a detection path; and
   (f) a charge coupled device for detecting the spectrum.

27. The apparatus as claimed in claim 26, wherein the charge coupled device produces a readout pattern that can be changed in real-time by reformatting (a) a number of simultaneous detection channels, and (b) a spectral bandpass of at least one of the one or more detection channels.

28. The apparatus as claimed in claim 26, further comprising a pinhole at an internal focal plane of the at least one afocal lens pair, wherein the pinhole prevents a substantial portion of light emifted from outside the focal plane of the excitation source from reaching the spectrograph.

29. The apparatus as claimed in claim 26, wherein the objective, the at least one afocal lens pair, and the spectrograph provide a magnification appropriate to image the scanned particles onto a two-dimensional surface of the charge coupled device.

30. The apparatus as claimed in claim 26, wherein the spectrograph comprises a concave holographic grating.

31. The apparatus as claimed in claim 26, wherein the spectrograph is adapted for a spectral range of 200 nm or more beginning from a wavelength of the excitation source and continuing to longer wavelengths.

32. The apparatus as claimed in claim 26, wherein a readout pattern of the charge coupled device can be changed in real-time by reprogramming one or more clock-drivers of the charge coupled device.

33. The apparatus as claimed in claim 26, wherein the charge coupled device is positioned in a focal plane of the spectrograph such that a dispersion direction is oriented substantially parallel to readout registers and shift registers of the charge coupled device.

34. The apparatus as claimed in claim 26, wherein, except for the spectrum of the collected emission light emitted by the sample in response to the excitation source, the charge coupled device is shielded from substantially all light.

35. The apparatus as claimed in claim 26, wherein the excitation source comprises a helium-neon gas laser having a wavelength of about 632.8 nm, and wherein the charge coupled device is optimal for a wavelength range of between about 620 nm and 850 nm, and wherein the sample comprises whole blood.

36. The apparatus as claimed in claim 26, wherein the scanner comprises a raster scanner.

37. The apparatus as claimed in claim 36, wherein a galvanometer-mirror implements one axis of the raster-scan across a surface of the sample.

38. The apparatus as claimed in claim 26, wherein the objective comprises an F-Theta scan lens to focus the excitation source into the sample and confocally collect the light emitted in response to the delivered excitation source.

39. The system as claimed in claim 38, wherein the F-Theta scan lens comprises a focal length of about 6.8 mm, a numerical aperture of about 0.55, and a magnification of about 20.

* * * * *

UNITED STATES PATENT AND TRADEMARK OFFICE
CERTIFICATE OF CORRECTION

PATENT NO. : 7,248,360 B2
APPLICATION NO. : 11/090673
DATED : July 24, 2007
INVENTOR(S) : Horchner et al.

It is certified that error appears in the above-identified patent and that said Letters Patent is hereby corrected as shown below:

Title should read --Polychromic Laser Scanning System and Method of Use--. It currently reads "Polychronic Laser Scanning System and Method of Use"

Signed and Sealed this

Thirtieth Day of October, 2007

JON W. DUDAS
*Director of the United States Patent and Trademark Office*